US007141696B2

(12) United States Patent
Aberg et al.

(10) Patent No.: US 7,141,696 B2
(45) Date of Patent: Nov. 28, 2006

(54) SMOOTH MUSCLE SPASMOLYTIC AGENTS

(75) Inventors: A. K. Gunnar Aberg, Sarasota, FL (US); Jan L. Chen, Shrewsbury, MA (US); Andrew T. Maioli, Warwick, RI (US); George E. Wright, Worchester, MA (US)

(73) Assignee: Bridge Pharma, Inc., Sarasota, FL (US)

( * ) Notice: Subject to any disclaimer, the term of this patent is extended or adjusted under 35 U.S.C. 154(b) by 60 days.

(21) Appl. No.: 10/850,868

(22) Filed: May 21, 2004

(65) Prior Publication Data

US 2004/0248987 A1   Dec. 9, 2004

Related U.S. Application Data

(60) Provisional application No. 60/473,173, filed on May 23, 2003.

(51) Int. Cl.
| C07C 211/03 | (2006.01) |
| C07C 211/04 | (2006.01) |
| C07C 211/05 | (2006.01) |
| C07C 211/06 | (2006.01) |
| C07C 211/07 | (2006.01) |
| C07C 211/08 | (2006.01) |
| A61K 31/135 | (2006.01) |

(52) U.S. Cl. ................................. 564/316; 514/648
(58) Field of Classification Search .............. None
See application file for complete search history.

(56) References Cited

U.S. PATENT DOCUMENTS

| 3,536,809 | A | 10/1970 | Applezweig | 424/28 |
| 3,598,123 | A | 8/1971 | Zaffaroni | 128/268 |
| 3,845,770 | A | 11/1974 | Theeuwes et al. | 128/260 |
| 3,916,899 | A | 11/1975 | Theeuwes et al. | 128/260 |
| 4,008,719 | A | 2/1977 | Theeuwes et al. | 128/260 |
| 5,236,956 | A | 8/1993 | Sjogren et al. | 514/617 |
| 5,382,600 | A * | 1/1995 | Jonsson et al. | 514/603 |
| 5,559,269 | A | 9/1996 | Johansson et al. | 564/443 |
| 5,686,464 | A | 11/1997 | Johansson et al. | 514/315 |
| 6,071,970 | A | 6/2000 | Mueller et al. | 514/648 |
| 6,087,346 | A | 7/2000 | Glennon et al. | 514/65 |
| 6,310,103 | B1 | 10/2001 | Aberg | 514/741 |
| 6,313,132 | B1 * | 11/2001 | Johansson et al. | 514/277 |

FOREIGN PATENT DOCUMENTS

| EP | 0957073 | 11/1999 |
| WO | 9220377 | 11/1992 |
| WO | 01/36375 | 5/2001 |
| WO | WO03/002059 | * 1/2003 |

OTHER PUBLICATIONS

Database CAPLUS on STN, Acc. No. 1997:132773, Mueller et al., WO 9640097 (Dec. 19, 1996) (abstract).*
Database CAPLUS on STN, Acc. No. 1995:200461, Nemeth et al., WO 9418959 (Sep. 1, 1994) (abstract).*
Database CAPLUS on STN, Acc. No. 1977:55074, Gueremy et al., DE 2617486 (Nov. 4, 1976) (abstract).*
Database CAPLUS on STN, Acc. No. 1974:433148, Eckhardt et al., Pahlavi Medical Journal (1973), 4(4), p. 461-476.*
Database CAPLUS on STN, Acc. No. 1969:96281, Blank et al., Journal of Medicinal Chemistry (1969), 12(2), p. 271-276.*
Database CAPLUS on STN, Acc. No. 1970:12330, Cho, US 3468951 (Sep. 23, 1969) (abstract).*
Database CAPLUS on STN, Acc. No. 1976:446175, Fujumura et al., JP 51016625 (Feb. 10, 1976) (abstract).*
Database CAPLUS on STN, Acc. No. 1975:3960, Fujimura et al., DE 2412798 (Sep. 26, 1974) (abstract).*
Database CAPLUS on STN, Acc. No. 1984:448177, Maryanoff et al., Journal of Medicinal Chemistrry (1984), 27(8), p. 1067-1071 (abstract).*
Database CAPLUS on STN, Acc. No. 1976:523557, Molloy, DE 2557182 (Jul. 1, 1976) (abstract).*
Database CAPLUS on STN, Acc. No. 1981:191089, Giumanini et al., European Journal of Mass Spectrometry in Biochemistry, Medicine and Environmental Research (1980), 1(2), p. 107-116 (abstract).*
Database CAPLUS on STN, Acc. No. 1989:533740, Devries et al., Journal of Medicinal Chemistry (1989), 32(10), p. 2318-2325 (abstract).*
Database CAPLUS on STN, Acc. No. 1977:21781, Molloy, US 3987201 (Oct. 10, 1976) (abstract).*
Database CAPLUS on STN, Acc. No. 2002:575060, Deprez et al., WO 2002059102 (Aug. 1, 2002) (abstract).*
Database CAPLUS on STN, Acc. No. 1998:515932, Miyachi et al., Bioorganic & Medicinal Chemistry Letters (1998), 8(14), p. 1807-1812 (abstract).*
Database CAPLUS on STN, Acc. No. 1962:455898, Easton et al., Journal of Organic Chemistry (1962), 27, p. 2746-2748 (abstract).*
Database CAPLUS on STN, Acc. No. 1977:21781, Molloy, US 3987201 (Oct. 19, 1976) (abstract).*
Database CAPLUS on STN, Acc. No. 1977:534477, Molloy, US 4034011 (Jul. 5, 1977) (abstract).*

(Continued)

*Primary Examiner*—Brian Davis
(74) *Attorney, Agent, or Firm*—Nields & Lemack

(57) ABSTRACT

The present invention relates to smooth muscle spasmolytic agents, pharmaceutical compositions containing them and method of using said compounds and compositions for the treatment of urinary incontinence, and other smooth muscle contractility conditions. More particularly, the present invention relates to certain metabolically stabilized secondary amines having smooth muscle relaxing properties while avoiding, on administration to a mammal, adverse side effects such as prominent antimuscarinic, arrhythmogenic and cardiodepressive effects.

17 Claims, No Drawings

OTHER PUBLICATIONS

Database CAPLUS on STN, Acc. No. 2003:30086, Zhou et al., Zhongguo Yaowu Huaxue Zazhi (2002), 12(3), p. 138-140 (abstract).*

Database CAPLUS on STN, Acc. No. 1998:682217, Johansson et al., WO9843942, Oct. 8, 1998 (abstract).*

Acta Physiol. Scand. 1965. 64. 15-27; A.K. G. Aberg et al. ;"Some Mechanical Aspects of an Intestinal Smooth Muscle".

J.Org. Chem. 1998, 63; 8067-8070; Andersson et al.; "Asymmetric Total Synthesis of (+)-Tolterodine, a New Muscarinic Receptor Antagonist, via Copper-Assisted Asymmetric Conjugate Addition of Aryl Grignard Reagents to 3-Phenyl-prop-2-enoyl-oxazolidinones".

Drug Metabolism and Disposition 1998, 26: 528-535; Andersson et al.; "Biotransformation of Tolterodine, a New Muscarinic Receptor Antagonist, in Mice, Rates and Dogs".

International Journal of Chemical Pharmacology and Therapeutics, vol. 35 No. 7—1997 (287-295); Brynne et a.; "Pharmacokinetics and pharmacodynamics of tolterodines in man: a new drug for the treatment of urinary bladder overactivity".

J. Urol. 1997, 157: Gillberg, P-G et al; Pharmacological profile of DD01 and desethyloxybutynin (DEOB)-the major metabolite of tolterodine and oxybutynin ABSTRACT 312.

J. Org. Chem. 1993, 58, 766-770; Nicolas et al.; "Asymmetric 1,4-Addition of Organocuprates to Chiral $\alpha,\beta$-Unsaturated N-Acyl-4-phenyl-2-oxazolidinones: A New Approach to the Synthesis of Chiral $\beta$-Branched CarboyxlicAcids".

Pharmacology & Toxicology 1997, 81, 169-172; Lisbeth Nilvebrant et al.; "Antimuscarinic Potency and Bladder Selectivity of PNU-200577, a Major Metabolite of Tolterodine".

Drug Metab Dispos, 26(4) 289-93 1998 Abstract; Postlind H, et al.; "Tolterodine, a new muscarinic receptor antagonist, is metabolized by cytochromes P450 2D6 and 3A in human liver microsomes".

Arzneim-Forsch./Drug Res. 48 (II), 10, 1012-1018 (1989); Emil R. Smith et al.; "Comparison of the Antimuscarinic and Antispasmodic Actions of Racemic Oxybutynin and Desethyloxybutynin and Their Enantiomers with Those of Racemic Terodiline".

Journal of Neurochemistry vol. 32, pp. 1653-1663; Chang et al.; "Heterogeneity of Histamine H1-Receptors: Species Variations in [3H] Mephyramine Binding of Brain Membranes".

Copy of the International Search Report dated Dec. 1, 2004.

* cited by examiner

SMOOTH MUSCLE SPASMOLYTIC AGENTS

RELATED US APPLICATION DATA

This application claims priority of Provisional Patent Application Ser. No. 60/473,173, filed on May 23, 2003, the disclosure of which is hereby incorporated by reference.

FIELD OF THE INVENTION

This invention relates to a series of new chemical entities that are in part structurally related to a compound named tolterodine having the formula:

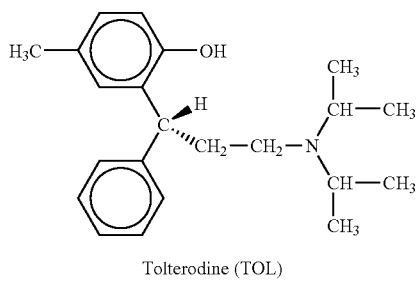

Tolterodine (TOL)

The generic name TOLTERODINE (CAS-124937-51-1; INN) refers to the R-enantiomer of the drug. In this document, the racemate and the S-isomer of the compound are referred to as RS-tolterodine (or RS-TOL) and S-tolterodine (or S-TOL), respectively. The R-isomer (tolterodine), whose chemical name is R—N,N-diisopropyl-3-(2-hydroxy-5-methylphenyl)-3-phenylpropylamine, is here referred to as TOL. Des-isopropyl-tolterodine is a metabolite of TOL and is here referred to as DES-TOL and the racemate and the S-isomer thereof are referred to as RSDES-TOL and SDES-TOL, respectively. The chemical name for RSDES-TOL is (R,S)—N-Isopropyl-3-(2-hydroxy-5-methylphenyl)-3-phenylpropylamine. The TOL metabolite 5-hydroxymethyl-tolterodine is here referred to as 5-HM and the racemate and the S-isomer thereof are referred to as RS5-HM and S5-HM, respectively. The chemical name for RS5-HM is RS5-N,N-diisopropyl-3-[2-hydroxy-5-hydroxymethyl)phenyl]-3-phenylpropylamine.

Specifically, the invention relates to new spasmolytic compounds and to methods of using said compounds for treating spasms of smooth muscle, such as for example smooth muscle of the urinary tract, smooth muscle of the gastrointestinal tract and smooth muscle of the respiratory tract. Smooth muscle hyperactivity includes for example various arterial and venous smooth muscle constrictions, spasms of the urinary tract, including smooth muscle spasms in connection with urolithiasis and urinary incontinence and pollakiuria, spasms of the gastrointestinal tract including esophageal and other intestinal spasms, such as diarrhea, irritable bowel syndrome and spasms in connection with gallbladder obstruction (cholelithiasis) or bile duct obstruction (choledocholithiasis). Spasms of the respiratory tract include smooth muscle contractions in connection with for example asthma, bronchitis and COPD (chronic obstructive pulmonary disease). The term "spasm" as used in this document includes smooth muscle contractility, caused by either hyperactivity or hyperreactivity.

In another embodiment, the compounds of the invention are useful in the treatment of cardiac disease, such as for example heart failure and cardiac arrhythmias, angina pectoris (stable angina and angina due to coronary artery spasms), atrial or ventricular tachycardia and ventricular extra-systolic heart beats.

The present invention is also directed to a method for reducing pain, such as for example pain caused by smooth muscle spasms, including pain induced by kidney or gall stones, the method comprising administering an effective amount of a compound of the present invention or an optically active isomer thereof, or a pharmaceutical composition containing a compound of the present invention to a patient in need of such treatment.

The present invention is still further directed to a method for the treatment of lower urinary tract symptoms (LUTS), which include but are not limited to bladder filling symptoms, such as urgency, incontinence, pollakiuria and nocturia, as well as voiding problems such as weak stream, hesitance, intermittency, incomplete bladder emptying and abdominal straining, the method comprising administering an effective amount of a compound of the present invention or an optically active isomer thereof, or a pharmaceutical composition containing a compound of the present invention to a patient in need of such treatment, optionally further comprising the inclusion of one or more anticholinergic compounds which may be selected from the group consisting of tolterodine, oxybutynin, darifenacin, fesoterodine, alvameline, trospium and temiverine or an optically active isomer thereof.

The present invention is also directed to a method for the treatment of LUTS in females which include but are not limited to urinary bladder filling symptoms, urgency, incontinence, pollakiuria and nocturia as well as voiding problems such as weak stream, hesitance, intermittency, incomplete bladder emptying, and abdominal straining, the method comprising administering an effective amount of a racemic or isomeric compound of the present invention or a pharmaceutical composition containing a compound of the present invention to a woman in need of such treatment, optionally further comprising the inclusion of one or more anticholinergic compounds which may be selected from the group consisting of tolterodine, oxybutynin, darifenacin, fesoterodine, alvameline, trospium and temiverine or an optically active isomer thereof.

BACKGROUND OF THE INVENTION

TOL has been shown to reduce bladder hyperactivity in patients suffering from urinary incontinence and exerts a spasmolytic effect on bladder smooth muscle by inhibiting the action of acetylcholine on smooth muscle. TOL has selectivity for muscarinic receptors over nicotinic acetylcholine receptors and as a result, no blocking effects are observed at skeletal neuromuscular junctions. Like TOL, the active metabolite of TOL, called 5HM, exerts potent and non-selective inhibition of muscarinic receptors (Gillberg, P-G & Sundquist S.: Pharmacological profile of DD01 and desethyloxybutynin (DEOB)—the major metabolite of tolterodine and oxybutynin. J. Urol. 1997, 157: Abstract 312.)

The compounds DES-TOL and 5-HM have been described as major metabolites of TOL by several investigators, such as for example Nilvebrant et al. 1997 (Antimuscarinic potency and bladder selectivity of PNU-200577, a major metabolite of tolterodine. Pharmacol Toxicol 81:169–172), Brynne et al. 1997 (Pharmacokinetics and pharmacodynamics of tolterodine in man: a new drug for the treatment of urinary bladder overactivity. Int J Clin Pharmacol Ther 35: 287–295), Andersson et al. 1998 (Biotransformation of tolterodine, a new muscarinic antagonist, in mice, rats, and dogs. Drug Metab Dispos. 26:528–535) and Postlind et al 1998 (Tolterodine, a new muscarinic receptor antagonist, is metabolized by cytochromes P450 2D6 and 3A in human liver microsomes. Drug Metab Dispos 26: 289–293).

Prodrugs or precursors of various types, such as for example of the type described by Sparf et al (EP 0957 073 A1) for the active metabolite of TOL, can be prepared for the compounds of the present invention by persons knowledgeable in the art of synthetic chemistry and such prodrugs or precursors are included in the present invention.

Work on non-cholinergic drugs for urinary incontinence has resulted in the compound S-TOL that was found to express non-cholinergic spasmolytic activities, while expressing little anticholinergic activity at pharmacological dose-levels (U.S. Pat. No. 6,310,103). The secondary amine metabolite of tolterodine (des-isopropyl-tolterodine or DES-TOL and particularly the corresponding S-isomer) was found to express non-cholinergic spasmolytic activities while the anticholinergic activity was further decreased (U.S. patent Ser. No. 09/775,060). The present invention represents another important step since the compounds of the present invention have surprisingly been found to be potent spasmolytic compounds, while being completely free from anticholinergic effects in pharmacological dose levels. Additionally, the compounds of the present invention are surprisingly free from cardiovascular side effects.

In this document, an optically pure compound or a compound being substantially free from its distomer implies an optical purity of at least 96%, preferably better than 98%.

DETAILED DESCRIPTION OF THE INVENTION

It has now been found that compounds of the present invention are causing selective smooth muscle relaxation, which in this case means that they inhibit smooth muscle contractions of the urinary tract, the gastrointestinal tract (including the gall bladder and connecting ducts), the pulmonary tract, and the uterus, while not causing hypotension or cardiac side effects. Furthermore, the new compounds prevent the occurrence of cardiac events, such as infarcts and will also prevent further cardiac deterioration in patients suffering from heart failure and using compounds of the present invention will also prevent the occurrence of atrial and ventricular tachycardia, as well as cardiac arrhythmias. Importantly, the new compounds will exert cardioprotective effects without causing hypotension with or without concomitant cardiac chronotropic, inotropic or dromotropic side effects.

It has now been found that compounds of this invention have surprisingly potent smooth muscle spasmolytic activities. It has now very surprisingly been found that the (S)-isomers of said compounds retain the spasmolytic activity of the corresponding distomer, while being completely free from muscarinic side effects. The R-isomers express a combination of spasmolytic calcium antagonistic activity and relatively weak antimuscarinic activity.

It has also surprisingly been found that compounds of the present invention, in addition to being potent and selective spasmolytic agents without antimuscarinic side effects, surprisingly express pronounced metabolic stability to human hepatic degradation, which translates into long drug half-lives in human patients, who may therefore only need to take their medication once or twice daily.

The compounds of the invention have been found to potently relax smooth muscle of the urinary bladder and are therefore effective in patients suffering from urinary incontinence, particularly urinary urge incontinence.

The compounds of the invention have been found to potently relax smooth muscle of the intestinal tract and are therefore effective in patients suffering from intestinal smooth muscle hyperactivity disorders, such as for example diarrhea and Irritable Bowel Syndrome (IBS).

The compounds of the invention have been found to potently relax smooth muscle of the respiratory airways and are therefore effective in patients suffering from constricted airways, in patients suffering from asthma, bronchitis or obstructive pulmonary diseases, such as for example COPD.

The compounds of the invention have been found to potently relax smooth muscle of the kidney and the urethers and are therefore effective in patients suffering from urolithiasis.

The compounds of the invention have been found to potently relax smooth muscle of the uterus and are therefore effective in patients suffering from tocolysis or dysmenorrhea.

The compounds of the invention have been found to potently relax smooth muscle of the gall bladder and the connecting ducts and are therefore effective in patients suffering from cholelithiasis or choledocholithiasis.

Surprisingly, and contrary to the secondary amine terodiline, the compounds of the present invention—although secondary amines—do not cause a delay of the cardiac repolarization, which is seen as prolongation of the QTc interval of the ECG and which is known to be the leading reason for a type of fatal cardiac ventricular arrhythmias, called Torsades de Pointe. Tolterodine potently prolongs the QTc interval and the incontinence medication terodiline (Micturine®)—like the antihistaminic medications terfenadine (Seldane®) and astemizole (Hismanal®)—were withdrawn from the market because of QTc prolongation and increased risks for Torsades de Pointes arrhythmias.

Compounds of the invention have the following formula (I):

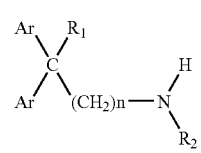

Formula I including stereochemically isomeric forms thereof and pharmaceutically acceptable salts thereof, wherein:

Ar represents a phenyl group, each of which may be optionally and independently substituted with A and/or B, A being ethyl or n-propyl, isopropyl, butyl, isobutyl, sec-butyl, t-butyl or hydroxymethyl, hydroxyethyl, hydroxypropyl, hydroxybutyl, and B being H, hydroxy or lower (1–3) alkoxy;

$R_1$ is hydrogen or lower alkyl;

$R_2$ is methyl, ethyl, n-propyl, isopropyl, butyl, isobutyl, sec-butyl or t-butyl, and n is 2–4.

PREFERRED EMBODIMENTS

Preferred compounds of Formula (I) include, but are not limited to, the following examples. The compounds may be in the form of their free bases or salts such as, but not limited to, hydrochlorides.

Example 1. RS—N-Isopropyl-3-(2-hydroxy-5-ethylphenyl)-3-phenylpropylamine

Example 2. R—N-Isopropyl-3-(2-hydroxy-5-ethylphenyl)-3-phenylpropylamine

Example 3. S—N-Isopropyl-3-(2-hydroxy-5-ethylphenyl)-3-phenylpropylamine

Example 4. RS—N-Isopropyl-3-(2-hydroxy-5-propylphenyl)-3-phenylpropylamine

Example 5. R—N-Isopropyl-3-(2-hydroxy-5-propylphenyl)-3-phenylpropylamine

Example 6. S—N-Isopropyl-3-(2-hydroxy-5-propylphenyl)-3-phenylpropylamine

Example 7. RS—N-Isopropyl-3-(2-hydroxy-5-isopropylphenyl)-3-phenylpropylamine

Example 8. R—N-Isopropyl-3-(2-hydroxy-5-isopropylphenyl)-3-phenylpropylamine

EXAMPLE 9. S—N-Isopropyl-3-(2-hydroxy-5-isopropylphenyl)-3-phenylpropylamine

Example 10. RS—N-Isopropyl-3-(2-hydroxy-5-butylphenyl)-3-phenylpropylamine

Example 11. R—N-Isopropyl-3-(2-hydroxy-5-butylphenyl)-3-phenylpropylamine

Example 12. S—N-Isopropyl-3-(2-hydroxy-5-butylphenyl)-3-phenylpropylamine

Example 13. RS—N-Isopropyl-3-(2-hydroxy-5-t-butylphenyl)-3-phenylpropylamine

Example 14. R—N-Isopropyl-3-(2-hydroxy-5-t-butylphenyl)-3-phenylpropylamine

Example 15. S—N-Isopropyl-3-(2-hydroxy-5-t-butylphenyl)-3-phenylpropylamine

Example 16. RS—N-Isopropyl-3-(2-hydroxy-5-hydroxymethylphenyl)-3-phenylpropylamine Example 17. R—N-Isopropyl-3-(2-hydroxy-5-hydroxymethylphenyl)-3-phenylpropylamine Example 18. S—N-Isopropyl-3-(2-hydroxy-5-hydroxymethylphenyl)-3-phenylpropylamine

Synthetic Chemistry

The compounds of the invention have been made as follows or have been made by methods similar hereto. All starting materials, reagents and solvents are commercially available. In all cases examples are isolated and characterized as the hydrochlorides. The General Methods for synthesis of racemic (RS) compounds are described in detail for Examples 1 and 13, and for synthesis of enantiomeric (R and S) compounds are described in detail for Examples 2 and 3, and 15.

General Method for Synthesis of Racemic Compounds

COMPOUND OF EXAMPLE 1

RS—N-Isopropyl-3-(2-hydroxy-5-ethylphenyl)3-phenylpropylamine Hydrochloride

Step 1. (±)-6-Ethyl-4-phenyl-3,4-dihydrocoumarin. A mixture of trans-cinnamic acid (15.1 g, 102 mmol), p-ethylphenol (8.3 g, 68 mmol), and sulfuric acid (4.15 mL), was heated to 130–135° C. After 1.5 hours, the mixture was cooled, partitioned between diethyl ether (400 mL) and water (150 mL), washed with water (1×80 mL) and 10% aqueous $K_2CO_3$ (3×100 mL), dried over $Na_2SO_4$, and evaporated giving an oil that was purified by column chromatography ($SiO_2$, petroleum ether:ethyl acetate 15:1–13:1–12:1–10:1). The fractions containing the product were pooled and evaporated giving 13 g (62%) of product: $^1$H NMR (300 MHz, $CDCl_3$) δ 7.39–7.24 (m, 7H), 7.20–7.01 (m, 1H), 4.31 (t, J=6.9 Hz, 1H), 3.11–2.95 (m, 2H), 2.55 (q, J=7.6 Hz, 2H), 1.16 (t, J=7.6, 3H).

Step 2. (±)-Methyl 3-(2-methoxy-5-ethylphenyl)-3-phenylpropionate. A solution of (±)-6-ethyl-4-phenyl-3,4-dihydrocoumarin (13 g, 51 mmol) in methanol (25 mL) and acetone (25 mL) containing methyl iodide (8 mL, 113 mmol) and $K_2CO_3$ (9:25 g, 67 mmol) was refluxed for 29 hours. The solvents were evaporated, and the residue was partitioned between diethyl ether (400 mL) and water (50 mL), washed with 20% $Na_2SO_3$ (2×100 mL), dried over $Na_2SO_4$, filtered and evaporated giving 13.4 g of an oil that was purified by column chromatography ($SiO_2$, petroleum ether:ethyl acetate 15:1–14:1). The appropriate fractions were pooled and evaporated giving 12.8 g (83%) of product: $^1$H NMR (300 MHz, $CDCl_3$) δ 7.29–7.10 (m, 5H), 7.04–6.94 (m, 2H), 6.78–6.71 (m, 1H), 4.37 (t, J=8.1 Hz, 1H), 3.74 (s, 3H), 3.57 (s, 3H), 3.09–3.02 (m, 2H), 2.54 (q, J=7.6 Hz, 2H), 1.17 (t, J=7.6 Hz, 3H).

Step 3. (±)-3-(2-Methoxy-5-ethylphenyl)-3-phenylpropanol. A solution of (±) methyl 3-(2-methoxy-5-ethylphenyl)-3-phenylpropionate (12.8 g, 42.9 mmol) in diethyl ether (25 mL) was treated dropwise with a solution of $LiAlH_4$ (1 M in diethyl ether, 34.5 mL, 34.5 mmol) over 20 minutes. The mixture was stirred overnight, then decomposed by the careful addition of water (1.5 g) and 15% NaOH until a white granular precipitate was formed (3 drops from Pasteur pipette). The mixture was diluted with diethyl ether (200 mL) and filtered. The filtrate was washed with water (3×100 mL), dried over $MgSO_4$, and evaporated giving an oil. The white granular salts were acidified with 2 N HCl (100 mL) and extracted with diethyl ether (100 mL). The ethereal layer was washed with water (3×100 mL), and with 10% $K_2CO_3$ (2×50 mL), dried over $Na_2SO_4$, and evaporated giving an oil. The oils were combined giving 12.5 g (100%) of crude product: $^1$H NMR (300 MHz, $CDCl_3$) δ 7.32–7.11 (m, 5H), 7.01–6.95 (m, 2H), 6.80–6.75 (m, 1H), 4.59 (t, J=8.0 Hz), 1H), 3.77 (s, 3H), 3.67–3.47 (m, 2H) 2.53 (q, J=7.6 Hz, 2H), 1.16 (t, J=7.6 Hz, 3H); $^{13}$C NMR (75 MHz, $CDCl_3$) δ 155.6, 145.2, 137.0, 133.2, 128.7, 127.7, 128.1, 126.7, 126.4, 111.4, 61.6, 56.2, 39.8, 38.3, 28.7, 16.4.

Step 4. (±)-3-(2-Methoxy-5-ethylphenyl)-3-phenylpropyl p-toluenesulfonate. A solution of (±)-3-(2-methoxy-5-ethylphenyl)-3-phenylpropanol (12.5 g, 44.4 mmol) in chloroform (45 mL) containing pyridine (14.4 mL, 178 mmol) was cooled to −10° C. and treated with p-toluenesulfonyl chloride (10.6 g, 55.5 mmol). After stirring for 3.5 hours, the mixture was poured into ice-water (200 mL) and stirred for 30 minutes. The organic phase was diluted with CH₂Cl₂ (100 mL), separated, washed with 10% K₂CO₃ (5 mL), water (50 mL), cold 2 N HCl (3×150 mL), water (150 mL), dried over Na₂SO₄, and placed under vacuum to remove solvent at a temperature no higher than 50° C. The resulting crude product weighed 20.7 g (100%) after being dried under high vacuum: ¹H NMR (300 MHz, CDCl₃) δ 7.78–7.71 (m, 2H), 7.34–7.12 (m, 7H), 7.04–6.94 (m, 2H), 6.78–6.72 (m, 1H), 4.45 (t, J=8.0 Hz, 1H), 4.09–3.94 (m, 2H), 3.74 (s, 3H), 2.57 (q, J=7.5 Hz, 2H), 2.48–2.31 (m, 5H), 1.20 (t, J=7.5 Hz, 3H); ¹³C NMR (75 MHz, CDCl₃) δ 156.5, 146.0, 144.8, 137.6, 134.6, 133.8, 131.2, 129.7, 129.4, 129.3, 128.6, 128.0, 127.6, 112.3, 70.6, 57.0, 41.1, 35.3, 29.6, 23.1, 17.4.

Step 5. (±)-N-Isopropyl-3-(2-methoxy-5-ethylphenyl)-3-phenylpropylamine. (±)-3-(2-Methoxy-5-ethylphenyl)-3-phenylpropyl p-toluenesulfonate (6.64 g, 15.2 mmol), isopropylamine (13 mL, 152 mmol), N,N-dimethylformamide (60 mL), activated 4 Angstrom molecular sieves [activated by pulverizing, and then heating to 180° C. for 1 hour under vacuum, 3.6 g], and cesium hydroxide monohydrate (2.55 g, 15.2 mmol) were combined and stirred in a sealed flask for 3 days. The solution was filtered over a pad of Celite, and rinsed with copious CH₂Cl₂. The filtrate was evaporated to dryness, the residue dissolved in diethyl ether (200 mL), washed with water (3×20 mL), 10% K₂CO₃ (50 mL), brine (30 mL), dried over Na₂SO₄, filtered and evaporated giving 4.48 g (91%) of crude product: ¹H NMR (300 MHz, CDCl₃) δ 7.33–6.93 (m, 7H), 6.79–6.71 (m, 1H), 4.43 (t, J=7.9 Hz, 1H), 3.74 (s, 3H), 2.76–2.66 (m, 1H), 2.55–2.31 (m, 4H), 2.28–2.12 (m, 2H), 1.17 (t, J=7.6 Hz, 3H), 0.99 (d, J=2.3 Hz, 3H), 0.97 (d, J=2.3 Hz, 3H); ¹³C NMR (75 MHz, CDCl₃) δ 155.5, 145.5, 136.5, 133.4, 128.6, 128.5, 127.7, 126.5, 126.2, 111.1, 55.8, 48.9, 46.5, 41.7, 36.1, 28.7, 23.5, 23.5, 16.4.

Step 6. (±)—N-Isopropyl-3-(2-hydroxy-5-ethylphenyl)-3-phenylpropylamine. A solution of (±)—N-isopropyl-3-(2-methoxy-5-ethylphenyl)-3-phenylpropylamine (4.47 g, 13.9 mmol) in CH₂Cl₂ (35 mL) was cooled to 0° C. and treated dropwise with a 1 M solution of BBr₃ in CH₂Cl₂ (14 mL, 14 mmol). After one hour at 0° C., the solution was stirred at room temperature for 1 hour, and then placed in the freezer overnight. The brown solution was made alkaline with 10% K₂CO₃ (100 mL), diluted with CH₂Cl₂, and the layers separated. The organic phase was treated with 2 N HCl (40 mL) and vigorously shaken, and then made alkaline with 10% K₂CO₃ (300 mL), washed with water (50 mL), dried over Na₂SO₄, filtered and evaporated giving 4.67 g (100%) crude product: ¹H NMR (300 MHz, CDCl₃) δ 7.36–7.17 (m, 5H), 6.92–6.84 (m, 2H), 6.52–6.46 (m, 1H), 4.63 (dd, J=12.6, 4.1 Hz, 1H), 2.94–2.75 (m, 2H), 2.51–2.10 (m, 5H), 1.17 (d, J=6.3 Hz, 3H), 1.12 (d, J=6.3 Hz, 3H), 1.04 (t, J=7.6, 3H); ¹³C NMR (75 MHz, CDCl₃) δ 154.8, 145.5, 136.0, 132.0, 129.0, 128.8, 128.6, 127.0, 126.6, 118.0, 49.0, 44.2, 40.0, 34.6, 28.7, 23.2, 21.9, 16.4.

Step 7. RS—N-Isopropyl-3-(2-hydroxy-5-ethylphenyl)-3-phenylpropylamine hydrochloride. A solution of (±)-N-isopropyl-3-(2-hydroxy-5-ethylphenyl)-3-phenylpropylamine (4.67 g, 15.1 mmol), in CH₂Cl₂ (100 mL) was treated with a solution of 4 N hydrogen chloride in dioxane (7.6 mL). The solvents were removed under vacuum, and the resulting precipitate was mixed with CH₂Cl₂, and the product was collected by suction filtration giving 3.84 g (73%) of product: mp 189–190° C.; ¹H NMR (300 MHz, DMSO-d₆) δ 9.28 (s, 1H), 1.88 (bs, 2H), 7.35–7.12 (m, 5H), 7.06–6.98 (m, 1H), 6.89–6.81 (m, 1H), 6.76–6.68 (m, 1H), 4.34 (t, J=7.4 Hz, 1H), 3.30–3.17 (m, 1H), 2.85–2.64 (m, 2H), 2.55–2.30 (m, 4H), 1.17 (d, J=6.4 Hz, 6H), 1.11 (t, J=7.6 Hz, 3H); ¹³C NMR (75 MHz, DMSO-d₆) δ 152.9, 144.4, 134.4, 129.7, 128.6, 128.1, 127.0, 126.6, 126.4, 115.6, 49.2, 43.1, 30.6, 27.9, 18.9, 18.8, 16.4.

COMPOUND OF EXAMPLE 13

RS—N-Isopropyl-3-(2-hydroxy-5-t-butylphenyl)-3-phenylpropylamine Hydrochloride

Step 1. (±)-6-t-Butyl 4-t-phenyl-3,4-dihydrocoumarin. A mixture consisting of trans-cinnamic acid (8.88 g, 60 mmol), 4-t-butylphenol (6.0 g, 40 mmol), and sulfuric acid (2.8 mL), was heated to (130–135° C.). After 1.5 h, the mixture was cooled, partitioned between ether (200 mL) and water (75 mL), washed with water (1×80 mL) and 10% K₂CO₃ (3×50 mL), dried over Na₂SO₄, and evaporated giving an oil that was purified by recrystallization from acetone. After storing in the freezer overnight, the resulting solid was collected by suction filtration and washed with petroleum ether, and dried under high vacuum resulting in 3.50 g (31%) of the title compound: ¹H NMR (300 MHz, DMSO-d₆) δ 7.40–7.23 (m, 5H), 7.19–7.12 (m, 2H), 7.11–7.05 (m, 1H), 4.51 (t, J=5.8 Hz, 1H), 3.20 (dd, J=16.0, 5.9 Hz, 1H), 3.04 (dd, J=16.0, 5.8 Hz, 1H), 1.21 (s, 9H); ¹³C NMR (75 MHz, DMSO-d₆) δ 168.2, 149.6, 147.3, 141.9, 129.2, 127.6, 127.5, 125.8, 125.6, 125.5, 116.5, 36.8, 34.5, 31.5, 31.0.

Step 2. (±)-Methyl 3-(2-methoxy-5-t-butylphenyl)-3-phenylpropionate. Following the procedure for Example 1, step 2, starting from (±)-6-t-butyl-4-phenyl-3,4-dihydrocoumarin (3.42 g, 12.2 mmol), iodomethane (3.8 mL, 61 mmol), acetone (9 mL), methanol (9 mL), and K₂CO₃ (2.20 g, 15.8 mmol) resulted in 3.78 g (greater than 100%) of the title compound. It was not purified and taken directly to the next step: ¹H NMR (300 MHz, CDCl₃) δ 7.36–7.10 (m, 7H), 6.82–6.71 (m, 1H), 4.90 (t, J=8.1 Hz, 1H), 3.73 (s, 3H), 3.57 (s, 3H), 3.16–3.02 (m, 2H), 1.26 (s, 9H); ¹³C NMR (75 MHz, CDCl₃) δ 172.9, 155.4, 144.1, 143.4, 131.7, 128.8, 128.5, 126.8, 125.6, 124.6, 111.0, 55.9, 51.9, 41.7, 40.2, 34.7, 32.1.

Step 3. (±)-3-(2-Methoxy-5-t-butylphenyl)-3-phenylpropanol. Following the general procedure for example 1, step 3, starting from (±)-methyl 3-(2-methoxy-5-t-butylphenyl)-3-phenylpropionate (3.93 g, 12.0 mmol), lithium aluminum hydride (1M in THF, 12 mL, 12 mmol), and THF (24 mL) gave 3.78 g (100%) of the title compound: ¹H NMR (300 MHz, CDCl₃) δ 7.32–7.10 (m, 7H), 6.81–6.74 (m, 1H), 4.58 (t, J=7.8 Hz, 1H), 3.78 (s, 3H), 3.68–3.49 (m, 2H), 2.41–2.16 (m, 2H), 1.65–1.59 (m, 1H), 1.25 (s, 9H); ¹³C NMR (75 MHz, CDCl₃) δ 155.5, 145.4, 143.8, 132.9, 128.8, 126.5, 125.7, 124.3, 111.0, 61.6, 56.1, 40.5, 38.5, 34.8, 32.3.

Step 4. (±)-3-(2-Methoxy-5-t-butylphenyl)-3-phenylpropyl p-toluenesulfonate. Following the general procedure for Example 1, step 4, starting from (±)-3-(2-methoxy-5-t-butylphenyl)-3-phenylpropanol (3.43 g, 11.5 mmol), p-tosyl chloride (2.63 g, 13.8 mmol), dichloromethane (12 mL), and pyridine (3.7 mL, 46 mmol) gave 4.29 g (85%) of the title compound after trituration of the resulting crude oil (obtained from methylene chloride) with petroleum ether: ¹H NMR (300 MHz, CDCl₃) δ 7.76–7.66 (m, 2H), 7.32–7.05 (m, 9H), 6.75–6.69 (m,1H), 4.41 (t, J=8.1 Hz, 1H), 4.04–3.90 (m, 2H), 3.70 (s, 3H), 2.44–2.28 (in, 2H), 1.24 (s, 9H); $^{13}$C NMR (75 MHz, CDCl$_3$) δ 155.4, 145.1, 144.1, 143.4, 133.8, 131.3, 130.4, 128.9, 128.6, 128.3, 126.7, 125.2, 124.7, 111.1, 69.7, 55.8, 40.06, 34.6, 32.2, 31.7, 21.9.

Step 5. (±)-N-Isopropyl-3-(2-methoxy-5-t-butylphenyl)-3-phenylpropylamine. Following the general procedure of Example 1, step 5, starting from (±)-3-(2-methoxy-5-t-butylphenyl)-3-phenylpropyl p-toluenesulfonate (4.17 g, 9.51 mmol), CsOH.H$_2$O (1.68 g, 9.99 mmol), activated 3 Angstrom molecular sieves (2.3 g), dry DMF (38 mL) and isopropylamine (12 mL, 143 mmol) gave 3.05 g (91%) of the title compound: $^1$H NMR (300 MHz, CDCl$_3$) δ 7.31–7.09 (m, 7H), 6.78–6.71 (m, 1H), 4.41 (t, J=7.9 Hz, 1H), 3.74 (s, 3H), 2.77–2.44 (m, 3H), 2.28–2.13 (m, 2H), 1.27 (s, 9H), 0.99 (d, J=4.2, 3H), 0.97 (d, J=4.2 Hz, 3H); $^{13}$C NMR (75 MHz, CDCl$_3$) δ 155.3, 145.5, 143.3, 132.9, 128.6, 128.5, 126.2, 125.4, 124.0, 110.6, 55.7, 48.9, 46.5, 42.2, 36.2, 34.6, 32.1, 23.5.

Step 6. (±)-N-Isopropyl-3-(2-hydroxy-5-t-butylphenyl)-3-phenylpropylamine. Following the general procedure of Example 1, step 6, starting from (±)-N-isopropyl-3-(2-methoxy-5-t-butylphenyl)-3-phenylpropylamine (1.71 g, 4.87 mmol), BBr$_3$ (1 M in CH$_2$Cl$_2$ 5.8 mL, 5.8 mmol), and CH$_2$Cl$_2$ (11 mL) gave 1.78 g (greater than 100%) of the title compound: $^1$H NMR (300 MHz, CDCl$_3$) δ 7.34–7.28 (m, 4H), 7.24–7.16 (m, 1H), 7.08–7.02 (m, 1H), 6.87–6.81 (m, 1H), 6.71–6.66 (m, 1H), 4.62 (dd, J=12.4, 4.0 Hz, 1H), 2.94–2.76 (m, 2H), 2.50–2.40 (m, 1H), 2.36–2.10 (m, 2H), 1.17 (d, J=6.3 Hz, 3H), 1.13 (d, J=6.3 Hz, 3H), 1.10 (s, 9H); $^{13}$C NMR (75 MHz, CDCl$_3$) δ 154.4, 145.3, 142.9, 131.2, 128.9, 128.6, 126.5, 126.3, 124.4, 117.4, 49.1, 44.1, 40.0, 34.6, 34.5, 32.0, 23.2, 21.8.

Step 7. (±)-N-Isopropyl-3-(2-hydroxy-5-t-butylphenyl)-3-phenylpropylamine hydrochloride. To a solution of (±)-N-isopropyl-3-(2-hydroxy-5-t-butylphenyl)-3-phenylpropylamine (1.59 g, 4.87 mmol) in CH$_2$Cl$_2$ (25 mL) was added hydrogen chloride (2 M in diethyl ether, 9.0 mL, 18 mmol). The resulting solution was reduced in volume to give an oil that did not fully dissolve in CH$_2$Cl$_2$, so methanol (5 mL) was added and it was stripped to give an oil, which was then taken up in CH$_2$Cl$_2$ (30 mL). When crystallization did not occur after 15 minutes, petroleum ether was added dropwise (about 3 mL), and shortly thereafter, crystallization slowly occurred. Three days later, the solid was collected, washed with 1:1 petroleum ether: CH$_2$Cl$_2$, and dried to give 1.27 g (72% for 2 steps) of the title compound: mp 207–208° C.; $^1$H NMR (300 MHz, DMSO-d$_6$) δ 7.33–7.26 (m, 4H), 7.20–7.13 (m, 2H), 7.05–6.99 (m, 1H), 6.74–6.68 (m, 1H); 4.34 (t, J=7.9 Hz, 1H), 3.34–3.17 (m, 1H), 2.86–2.63 (m, 2H), 2.43–2.25 (m, 2H), 1.22 (s, 9H), 1.16 (d, J=6.5 Hz, 6H); $^{13}$C NMR (75 MHz, DMSO-d$_6$) δ 152.7, 144.4, 141.4, 129.0, 128.6, 128.1, 126.4, 124.5, 123.9, 115.1, 49.2, 43.1, 41.4, 40.7, 34.1, 31.8, 30.6, 18.9, 18.8.

The general processes for Examples 1 and 13 were used to prepare additional examples, as follows.

COMPOUND OF EXAMPLE 4

RS—N-Isopropyl-3-(2-hydroxy-5-propylphenyl)-3-phenylpropylamine hydrochloride. Mp 175–177° C.; $^1$H NMR (300 MHz, DMSO-d$_6$) δ 9.28 (s, 1H), 8.91 (bs, 2H), 7.45–6.97 (m, 6H), 6.91–6.68 (m, 2H), 4.43–4.30 (m, 1H), 3.44–3.16 (m, 1H), 2.89–2.63 (m, 2H), 2.62–2.28 (m, 7H), 1.62–1.45 (m, 2H), 1.17 (d, J=6.4 Hz, 6H), 0.85 (t, J=7.4 Hz, 3H); $^{13}$C NMR (75 MHz, DMSO-d$_6$) δ153.0, 144.4, 132.8, 129.5, 128.6, 128.1, 127.6, 127.2, 126.3, 115.5, 49.3, 43.1, 41.1, 37.1, 30.6, 24.9, 18.9, 18.8, 13.9.

COMPOUND OF EXAMPLE 7

RS—N-Isopropyl-3-(2-hydroxy-5-isopropylphenyl)-3-phenylpropylamine hydrochloride. Mp 176–179° C.; $^1$H NMR (300 MHz, DMSO-d$_6$) δ 9.28 (s, 1H), 8.89 (bs, 2H), 7.33–7.13 (m, 5H), 7.09–7.03 (m, 1H), 6.92–6.85 (m, 1H), 6.76–6.69 (m, 1H), 4.34 (t, J=7.8 Hz, 1H), 3.31–3.18 (m, 1H), 2.84–2.64 (m, 2H), 2.43–2.30 (m, 2H), 1.17 (d, J=6.6 Hz, 6H), 1.14 (d, J=7.0 Hz, 6H); $^{13}$C NMR (75 MHz, DMSO-d$_6$) δ 153.1, 144.4, 139.2, 129.5, 128.6, 128.1, 126.3, 125.6, 124.9, 115.5, 49.2, 43.1, 33.1, 30.6, 24.7, 18.9, 18.8.

COMPOUND OF EXAMPLE 10

RS—N-Isopropyl-3-(2-hydroxy-5-butylphenyl)-3-phenylpropylamine hydrochloride. Mp 149–150° C.; $^1$H NMR (300 MHz, DMSO-d$_6$) δ 9.23 bs(1H), 8.85 (bs, 2H), 7.34–7.11 (m, 5H), 7.04–6.96 (m, 1H), 6.86–6.79 (m, 1H), 6.75–6.67 (m, 1H), 4.33 (t, J=7.8 Hz, 1H), 3.30–3.16 (m, 1H), 2.87–2.62 (m, 2H), 2.48–2.26 (m, 4H), 1.56–1.40 (m, 2H), 1.33–1.09 (m, 8H), 0.87 (t, J=7.3 Hz, 3H); $^{13}$C NMR (75 MHz, DMSO-d$_6$) δ 152.9, 144.4, 132.9, 129.5, 128.6, 128.1, 127.5, 127.1, 126.3, 115.5, 49.3, 43.1, 34.6, 34.0, 30.6, 22.1, 18.9, 18.8, 14.2.

General method for enantiomeric compounds

Enantiomeric compounds of the invention may be prepared by use of specific chiral synthons or chiral auxiliary catalysts, for example, as described by Andersson et al. (J. Org. Chem., 1998, 63, 8067). Alternatively, the enantiomeric compounds of the invention may be obtained by fractional crystallization of the racemic compounds, using chiral acids, such as, but not limited to, tartaric acids, dibenzoyltartaric acids, di-p-toluyltartaric acids or mandelic acids.

Examples of synthesis of enantiomeric compounds of the invention by the use of chiral auxiliaries are presented in detail for several preferred compounds.

COMPOUND OF EXAMPLE 2

R—N-Isopropyl-3-(2-hydroxy-5-ethylphenyl)-3-phenylpropylamine Hydrochloride

Step 1. (4R)-Phenyl-(3R)-(2-methoxy-5-ethylphenyl)-3-phenylpropanoyl-2-oxazolidinone. Activated magnesium (808 mg, 33.2 mmol; activated by stirring under high vacuum at 80° C. for 20 minutes) was added to a solution of 1-methoxy-2-bromo-4-ethylbenzene (6.2 g, 29 mmol) in anhydrous tetrahydrofuran (48 mL) at room temperature under N$_2$. After consumption of the Mg (about 1 hour), the resulting solution was added dropwise to a previously cooled (−40° C.) solution of CuBr-dimethylsulfide complex (2.97 g, 14.4 mmol), tetrahydrofuran (46 mL) and dimethylsulfide (21 mL) during 5 minutes. When the temperature in the cooling bath reached −25° C., a solution of (4R)-phenyl-N-cinnamyl-2-oxazolidinone (Nicolas et al., J. Org. Chem. 1993, 58, 766). (2.83 g, 9.63 mmol) in tetrahydrofuran (48 mL) was added dropwise during 30 minutes with the temperature being maintained between −20 and −25° C. When the addition was complete, the resulting biphasic reaction mixture was stirred for 2 hours, over the course of which the reaction slowly warmed to −10° C., and a solution eventually formed. The reaction was quenched by addition of 10% aqueous NH$_4$Cl (20 mL), and the organic solvents were removed in vacuo. The resulting material was dissolved in ethyl acetate (2×80 mL) and diethyl ether (2×40 mL). The organic extracts were combined, washed with 28% NH$_4$OH (2×50 mL), 17% NH$_4$OH (2×50 mL), water (50 mL), brine (50 mL), dried over Na$_2$SO$_4$, filtered, and evaporated to give an oil that was purified by chromatography (SiO$_2$, petroleum ether:ethyl acetate gradient, 8:14:1). The appropriate fractions were pooled and evaporated to give 3.437 g (83%) of product: $^1$H NMR (300 MHz, CDCl$_3$) δ 7.34 (m, 7H), 7.16–7.02 (m, 4H), 6.99–6.92 (m, 1H), 6.72–6.64 (m, 1H), 5.26–5.17 (m, 1H), 4.98 (dd, J=8.8, 6.4 Hz, 1H), 4.43 (t, J=8.7 Hz, 1H), 4.07 (dd, J=8.9, 6.5 Hz, 1H), 3.85 (dd, J=17.4, 8.9 Hz, 1H), 3.68–3.40 (m, 4H), 2.53 (q, =7.6 Hz, 2H), 1.16 (t, J=7.6 Hz, 3H);

Step 2. (3R)-(2-Methoxy-5-ethylphenyl)-3-phenylpropanol. To a solution of (4R)-phenyl-(3R)-(2-methoxy-5-ethylphenyl)-3-phenylpropanoyl-2-oxazolidinone (3.33 g, 7.75 mmol) in diethyl ether (155 mL) was added 1 equivalent of water (144 μL) followed by dropwise addition of a 2 M solution of LiBH$_4$ in tetrahydrofuran (4.07 mL, 8.14 mmol) over 15 minutes at 0° C. under N$_2$. When the reaction was complete (tlc, 1–2 hours), aqueous NaOH (2 N, 75 mL) was added carefully, and the volatiles were removed in vacuo. The resulting material was dissolved in 1:1 diethyl ether: ethyl acetate (150 mL) and washed with brine (50 mL), dried over Na$_2$SO$_4$, filtered and evaporated to give an oil that was purified by column chromatography (SiO$_2$, 3:1 petroleum ether:ethyl acetate). The appropriate fractions were pooled and concentrated to give 1.61 g, (76.6%) of product: $^1$H NMR (300 MHz, CDCl$_3$) δ 7.32–7.11 (m, 5H), 7.01–6.95 (m, 2H), 6.80–6.75 (m, 1H), 4.59 (t, I=8.0 Hz), 1H), 3.77 (s, 3H), 3.67–3.47 (m, 2H), 2.53 (q, J=7.6 Hz, 2H), 1.16 (t, J=7.6 Hz, 3H); $^{13}$C NMR (75 MHz, CDCl$_3$) δ 155.6, 145.2, 137.0, 133.2, 128.7, 127.7, 128.1, 126.7, 126.4, 111.4, 61.6, 56.2, 39.8, 38.3, 28.7, 16.4.

Step 3. (3R)-(2-Methoxy-5-ethylphenyl)-3-phenylpropyl p-toluenesulfonate. A solution of (3R)-(2-methoxy-5-ethylphenyl)-3-phenylpropanol (1.5 g, 5.56 mmol) in chloroform (6 mL) containing pyridine (1.81 mL, 22.2 mmol) was cooled to −10° C. and treated with p-toluene-sulfonyl chloride (1.32 g, 6.95 mmol). After stirring for 3.5 hours, the mixture was poured into ice-water (200 mL) and stirred for 30 minutes. The organic phase was diluted with CH$_2$Cl$_2$ (100 mL), separated, washed with 10% K$_2$CO$_3$ (5 mL), water (50 mL); cold 2 N HCl (3×150 mL), water (150 mL), dried over Na$_2$SO$_4$, and placed under vacuum to remove solvent at a temperature no higher than 50° C. The resulting crude oil was purified by column chromatography (SiO$_2$, 8:1–5:1 petroleum ether:ethyl acetate). The appropriate fractions were pooled and evaporated to give 2.248 g (95%) of product after drying under high vacuum: $^1$H NMR (300 MHz, CDCl$_3$) δ 7.78–7.71 (m, 2H), 7.34–7.12 (m, 7H), 7.04–6.94 (m, 2H), 6.78–6.72 (m, 1H), 4.45 (t, J=8.0 Hz, 1H), 4.09–3.94 (m, 2H), 3.74 (s, 3H), 2.57 (q, J=7.5 Hz, 2H), 2.48–2.31 (m, 5H), 1.20 (t, J=7.5 Hz, 3H); $^{13}$C NMR (75 MHz, CDCl$_3$) 156.5, 146.0, 144.8, 137.6, 134.6, 133.8, 131.2, 129.7, 129.4, 129.3, 128.6, 128.0, 127.6, 112.3, 70.6, 57.0, 41.1, 35.3, 29.6, 23.1, 17.4.

Step 4. N-Isopropyl-(3R)-(2-methoxy-5-ethylphenyl)-3-phenylpropylamine. (3R)-(2-Methoxy-5-ethylphenyl)-3-phenylpropyl p-toluenesulfonate (2.248 g, 4.23 mmol), isopropylamine (8.4 mL, 99 mmol), N,N-dimethylformamide (21 mL), activated 4 Angstrom molecular sieves [activated by pulverizing, and then heating to 180° C. for 1 hour under vacuum, 1.26 g], and cesium hydroxide monohydrate (1.11 g, 6.62 mmol) were combined and stirred in a sealed flask for 3 days. The solution was filtered over a pad of Celite, and rinsed with copious CH$_2$Cl$_2$. The filtrate was evaporated to dryness, and the residue was dissolved in diethyl ether (100 mL), washed with water (25 mL), 10% K$_2$CO$_3$ (2×50 mL), brine (30 mL), dried over Na$_2$SO$_4$, filtered and evaporated to give 1.637 g (96%) crude product: $^1$H NMR (300 MHz, CDCl$_3$) δ 7.33–6.93 (m, 7H), 6.79–6.71 (m, 1H), 4.43 (t, J=7.9 Hz, 1H), 3.74 (s, 3H), 2.76–2.66 (m, 1H), 2.55–2.31 (m, 4H), 2.28–2.12 (m, 2H), 1.17 (t, J=7.6 Hz, 3H), 0.99 (d, J=2.3 Hz, 3H), 0.97 (d, J=2.3 Hz, 3H); $^{13}$C NMR (75 MHz, CDCl$_3$) δ 155.5, 145.5, 136.5, 133.4, 128.6, 128.5, 127.7, 126.5, 126.2, 111.1, 55.8, 48.9, 46.5, 41.7, 36.1, 28.7, 23.5, 23.5, 16.4.

Step 5. R—N-Isopropyl-(2-hydroxy-5-ethylphenyl)-3-phenylpropylamine. A solution of N-isopropyl-(3R)-(2-methoxy-5-ethylphenyl)-3-phenylpropylamine (1.462 g, 4.53 mmol) in CH$_2$Cl$_2$ (10 mL) was cooled to 0° C. and treated dropwise with a 1 M solution of BBr$_3$ in CH$_2$Cl$_2$ (5.7 mL, 5.7 mmol). After 1 hour at 0° C., the solution was stirred at room temperature for 1 hour, and then placed in the freezer overnight. The brown solution was made alkaline with 10% K$_2$CO$_3$ (100 mL), diluted with CH$_2$Cl$_2$, and the layers separated. The organic phase was treated with 2 N HCl (30 mL) and vigorously shaken, and then made alkaline with 10% K$_2$CO$_3$ (300 mL), washed with water (50 mL), dried over Na$_2$SO$_4$, filtered and evaporated giving 1.399 g (100%) of crude product: $^1$H NMR (300 MHz, CDCl$_3$) δ 7.36–7.17 (m, 5H), 6.92–6.84 (m, 2H), 6.52–6.46 (m, 1H), 4.63 (dd, J=12.6, 4.1 Hz, 1H), 2.94–2.75 (m, 2H), 2.51–2.10 (m, 5H), 1.17 (d, I=6.3 Hz, 3H), 1.12 (d, J=6.3 Hz, 3H), 1.04 (t, I=7.6, 3H); $^{13}$C NMR (75 MHz, CDCl$_3$) δ 154.8, 145.5, 136.0, 132.0, 129.0, 128.8, 128.6, 127.0, 126.6, 118.0, 49.0, 44.2, 40.0, 34.6, 28.7, 23.2, 21.9, 16.4.

Step 6. R—N-Isopropyl-(2-hydroxy-5-ethylphenyl)-3-phenylpropylamine hydrochloride. A solution of N-isopropyl-(3R)-(2-hydroxy-5-ethylphenyl)-3-phenylpropylamine (1.40 g, 4.539 mmol) in CH$_2$Cl$_2$ (100 mL) was treated with a solution of 2 N hydrogen chloride in diethyl ether (20 mL). The solvents were removed under vacuum and the resulting material was dissolved in methanol. The methanol was evaporated to give a brown oil that was dissolved in CH$_2$Cl$_2$, and, upon standing, crystallization occurred. The white solid was collected by suction filtration and washed with CH$_2$Cl$_2$ to give 1.16 g (74%) of product, mp 145–148° C.; $^1$H NMR (300 MHz, DMSO-d$_6$) δ 9.28 (s, 1H), 1.88 (bs, 2H), 7.35–7.12 (m, 5H), 7.06–6.98 (m, 1H), 6.89–6.81 (m, 1H), 6.76–6.68 (m, 1H), 4.34 (t, I=7.4 Hz, 1H), 3.30–3.17 (m, 1H), 2.85–2.64 (m, 2H), 2.55–2.30 (m, 4H), 1.17 (d, J=6.4 Hz, 6H), 1.11 (t, J=7.6 Hz, 3H); $^{13}$C NMR (75 MHz, DMSO-d$_6$) δ 152.9, 144.4, 134.4, 129.7, 128.6, 128.1, 127.0, 126.6, 126.4, 115.6, 49.2, 43.1, 30.6, 27.9, 18.9, 18.8, 16.4; enantiomeric excess 99.4% (20 μL of a 3 mg/mL solution of the free base [generated from the hydrochloride] in 3:1 hexane:EtOH was injected onto a Chiralcel OD 250×4.6 mm HPLC column, mobile phase 95:5:0.1 hexane: ethanol:diethylamine, λ 285 nm, flow rate 1 mL/min, r$_t$=7.83 min).

COMPOUND OF EXAMPLE 3

S—N-Isopropyl-3-(2-hydroxy-5-ethylphenyl)-3-phenylpropylamine Hydrochloride

Step 1. (4S)-Phenyl-(3S)-(2-methoxy-5-ethylphenyl)-3-phenylpropanoyl-2-oxazolidinone. Activated magnesium (1.00 g, 41.2 mmol; activated by stirring under high vacuum at 80° C. for 20 minutes) was added to a stirred solution of 1-methoxy-2-bromo-4-ethylbenzene (7.70 g, 35.8 mmol) in anhydrous tetrahydrofuran (60 mL) at room temperature under $N_2$. After consumption of the Mg (about 1 hour), the resulting solution was added dropwise to a previously cooled (−40° C.) solution of CuBr-dimethylsulfide complex (3.68 g, 17.9 mmol), tetrahydrofuran (55 mL) and dimethylsulfide (25 mL) during 5 minutes. When the temperature in the cooling bath reached −25° C., a solution of (4S)-phenyl-N-cinnamyl-2-oxazolidinone (3.50 g, 11.9 mmol) in tetrahydrofuran (65 mL) was added dropwise during 30 minutes with the temperature being maintained between −20 and −25° C. When the addition was complete, the resulting biphasic reaction mixture was stirred for 2 hours, over the course of which the reaction slowly warmed to −10° C., and a solution eventually formed. The reaction was quenched by addition of 10% aqueous $NH_4Cl$ (30 mL), and the organic solvents were removed in vacuo. The resulting material was extracted with ethyl acetate (2×80 mL) and diethyl ether (2×40 mL). The organic extracts were combined, washed with 28% $NH_4OH$ (2×50 mL), 17% $NH_4OH$ (2×75 mL), water (2×50 mL), brine (50 mL), dried over $Na_2SO_4$, filtered, and evaporated to give an oil that was purified by chromatography ($SiO_2$, petroleum ether:ethyl acetate gradient, 8:1–4:1). The appropriate fractions were pooled and evaporated to give 4.97 g, (97%) of product: $^1$H NMR (300 MHz, $CDCl_3$) δ 7.34 (m, 7H), 7.16–7.02 (m, 4H), 6.99–6.92 (m, 1H), 6.72–6.64 (m, 1H), 5.26–5.17 (m, 1H), 4.98 (dd, J=8.8, 6.4 Hz, 1H), 4.43 (t, J=8.7 Hz, 1H), 4.07 (dd, J=8.9, 6.5 Hz, 1H), 3.85 (dd, J=17.4, 8.9 Hz, 1H), 3.68–3.40 (m, 4H), 2.53 (q, J=7.6 Hz, 2H), 1.16 (t, J=7.6 Hz, 3H);

Step 2. (3S)-(2-Methoxy-5-ethylphenyl)-3-phenylpropanol. To a solution of (4S)-phenyl-(3S)-(2-methoxy-5-ethylphenyl)-3-phenylpropanoyl-2-oxazolidinone (4.40 g, 10.2 mmol) in diethyl ether (255 mL) was added 1 equivalent of water (180 μL) followed by dropwise addition of a 2 M solution of $LiBH_4$ in tetrahydrofuran (5.36 mL, 10.7 mmol) during 15 minutes at 0° C. under $N_2$. When the reaction was complete (tlc, 1–2 hours), aqueous NaOH (2 N, 75 mL) was added carefully, and the volatiles were removed in vacuo. The resulting material was dissolved in 1:1 diethyl ether:ethyl acetate (150 mL) and washed with brine (50 mL), dried over $Na_2SO_4$, filtered and evaporated to give an oil that was purified by column chromatography ($SiO_2$, 3:1 petroleum ether:ethyl acetate). The appropriate fractions were pooled and concentrated to give 2.16 g, (78.0%), of product: $^1$H NMR (300 MHz, $CDCl_3$) δ 7.32–7.11 (m, 5H), 7.01–6.95 (m, 2H), 6.80–6.75 (m, 1H), 4.59 (t, J=8.0 Hz), 1H), 3.77 (s, 3H), 3.67–3.47 (m, 2H), 2.53 (q, J=7.6 Hz, 2H), 1.16 (t, J=7.6 Hz, 3H); $^{13}$C NMR (75 MHz, $CDCl_3$) δ 155.6, 145.2, 137.0, 133.2, 128.7, 127.7, 128.1, 126.7, 126.4, 111.4, 61.6, 56.2, 39.8, 38.3, 28.7, 16.4.

Step 3. (3S)-(2-Methoxy-5-ethylphenyl)-3-phenylpropyl p-toluenesulfonate. A solution of (3S)-(2-methoxy-5-ethylphenyl)-3-phenylpropanol (1.94 g, 7.18 mmol) in chloroform (7 mL) containing pyridine (2.32 mL, 28.7 mmol) was cooled to −10° C. and treated with p-toluenesulfonyl chloride (1.71 g, 8.98 mmol). After stirring for 3.5 hours, the mixture was poured into ice-water (200 mL) and stirred for 30 minutes. The organic phase was diluted with $CH_2Cl_2$ (100 mL), separated, washed with 10% $K_2CO_3$ (5 mL), water (50 mL), cold 2 N HCl (3×150 mL), water (150 mL), dried over $Na_2SO_4$, and placed under vacuum to remove solvent at a temperature no higher than 50° C. The resulting crude oil was purified by column chromatography ($SiO_2$, 8:1–5:1 petroleum ether:ethyl acetate). The appropriate fractions were pooled and evaporated to give 2.76 g (91%) of product after drying under high vacuum: $^1$H NMR (300 MHz, $CDCl_3$) δ 7.78–7.71 (m, 2H), 7.34–7.12 (m, 7H), 7.04–6.94 (m, 2H), 6.78–6.72 (m, 1H), 4.45 (t, J=8.0 Hz, 1H), 4.09–3.94 (m, 2H), 3.74 (s, 3H), 2.57 (q, J=7.5 Hz, 2H), 2.48–2.31 (m, 5H), 1.20 (t, J=7.5 Hz, 3H); $^{13}$C NMR (75 MHz, $CDCl_3$) δ 156.5, 146.0, 144.8, 137.6, 134.6, 133.8, 131.2, 129.7, 129.4, 129.3, 128.6, 128.0, 127.6, 112.3, 70.6, 57.0, 41.1, 35.3, 29.6, 23.1, 17.4.

Step 4. N-Isopropyl-(3S)-(2-methoxy-5-ethylphenyl)-3-phenylpropylamine. (3S)-(2-Methoxy-5-ethylphenyl)-3-phenylpropyl p-toluenesulfonate (2.76 g, 6.50 mmol), isopropylamine (6.13 mL, 72 mmol), N,N-dimethylformamide (29 mL), activated 4 Angstrom molecular sieves [activated by pulverizing, and then heating to 180° C. for 1 hour under vacuum, 1.74 g], and cesium hydroxide monohydrate (1.20 g, 7.18 mmol) were combined and stirred in a sealed flask for 3 days. The solution was filtered over a pad of Celite, and rinsed with copious $CH_2Cl_2$. The filtrate was evaporated to dryness, the residue dissolved in diethyl ether (100 mL), washed with water (25 mL), 10% $K_2CO_3$ (2×50 mL), brine (30 mL), dried over $Na_2SO_4$, filtered and evaporated to give 2.138 g (98%) of product: $^1$H NMR (300 MHz, $CDCl_3$) δ 7.33–6.93 (m, 7H), 6.79–6.71 (m, 1H), 4.43 (t, J=7.9 Hz, 1H), 3.74 (s, 3H), 2.76–2.66 (m, 1H), 2.55–2.31 (m, 4H), 2.28–2.12 (m, 2H), 1.17 (t, J=7.6 Hz, 3H), 0.99 (d, I=2.3 Hz, 3H), 0.97 (d, I=2.3 Hz, 3H); $^{13}$C NMR (75 MHz, $CDCl_3$) δ 155.5, 145.5, 136.5, 133.4, 128.6, 128.5, 127.7, 126.5, 126.2, 111.1, 55.8, 48.9, 46.5, 41.7, 36.1, 28.7, 23.5, 23.5, 16.4.

Step 5. S—N-Isopropyl-(2-hydroxy-5-ethylphenyl)-3-phenylpropylamine. A solution of N-isopropyl-(3S)-(2-methoxy-5-ethylphenyl)-3-phenylpropylamine (2.138 g, 6.632 mmol) in $CH_2Cl_2$ (15 mL) was cooled to 0° C. and treated dropwise with a 1 M solution of $BBr_3$ in $CH_2Cl_2$ (7.0 mL, 7.0 mmol). After one hour at 0° C., the solution was stirred at room temperature for 1 hour, and then placed in the freezer overnight. The brown solution was made alkaline with 10% $K_2CO_3$ (110 mL), diluted with $CH_2Cl_2$ and separated. The organic phase was treated with 2 N HCl (30 mL) and vigorously shaken, and then made alkaline with 10% $K_2CO_3$ (300 mL), washed with water (50 mL), dried over $Na_2SO_4$, filtered and evaporated giving 2.031 g (99%) of product: $^1$H NMR (300 MHz, $CDCl_3$) δ 7.36–7.17 (m, 5H), 6.92–6.84 (m, 2H), 6.52–6.46 (m, 1H), 4.63 (dd, J=12.6, 4.1 Hz, 1H), 2.94–2.75 (m, 2H), 2.51–2.10 (m, 5H), 1.17 (d, J=6.3 Hz, 3H), 1.12 (d, J=6.3 Hz, 3H), 1.04 (t, J=7.6 Hz, 3H); $^{13}$C NMR (75 MHz, $CDCl_3$) δ 154.8, 145.5, 136.0, 132.0, 129.0, 128.8, 128.6, 127.0, 126.6, 118.0, 49.0, 44.2, 40.0, 34.6, 28.7, 23.2, 21.9, 16.4.

Step 6. S—N-Isopropyl-(2-hydroxy-5-ethylphenyl)-3-phenylpropylamine hydrochloride. A solution of N-isopropyl-(3S)-(2-hydroxy-5-ethylphenyl)-3-phenylpropylamine (2.031 g, 6.584 mmol) in $CH_2Cl_2$ (32 mL) was treated with a solution of 2N hydrogen chloride in diethyl ether (10 mL). The solvents were removed under vacuum, and the resulting material was dissolved in methanol. The methanol was evaporated to give a brown oil that was dissolved in CH$_2$Cl$_2$ (50 mL), and, upon standing, crystallization occurred. The white solid was collected by suction filtration and washed with CH$_2$Cl$_2$ to give 1.365 g (60%) of product, mp 145–148° C.; $^1$H NMR (300 MHz, DMSO-d$_6$) δ 9.28 (s, 1H), 1.88 (bs, 2H), 7.35–7.12 (m, 5H), 7.06–6.98 (m, 1H), 6.89–6.81 (m, 1H), 6.76–6.68 (m, 1H), 4.34 (t, J=7.4 Hz, 1H), 3.30–3.17 (m, 1H), 2.85–2.64 (m, 2H), 2.55–2.30 (m, 4H), 1.17 (d, J=6.4 Hz, 6H), 1.11 (t, J=7.6 Hz, 3H); $^{13}$C NMR (75 MHz, DMSO-d$_6$) δ 152.9, 144.4, 134.4, 129.7, 128.6, 128.1, 127.0, 126.6, 126.4, 115.6, 49.2, 43.1, 30.6, 27.9, 18.9, 18.8, 16.4; enantiomeric excess 99.5% (20 μL of a 3 mg/mL solution of the free base [generated from the hydrochloride] in 3:1 hexane:ethanol was injected onto a Chiralcel OD 250×4.6 mm HPLC column, mobile phase 95:5:0.1 hexane: ethanol diethylamine, λ 285 nm, flow rate 1 mL/min, r$_t$=6.15 min).

COMPOUND OF EXAMPLE 15

S—N-Isopropyl-3-(2-hydroxy-5-t-butylphenyl)-3-phenyl-propylamine hydrochloride

Step 1. 1-Methoxy-2-bromo-4-t-butylbenzene. A solution of 4-t-butylphenol (50 g, 333 mmol) in chloroform (400 mL) was combined with NaHCO$_3$ (36 g, 428 mmol) and cooled to 0° C. under N$_2$. A solution of bromine (54.6 g, 342 mmol) in chloroform (90 mL) was added dropwise with stirring over 75 minutes. After 3 hours at 0° C., the reaction was treated with 20% aqueous Na$_2$SO$_3$ (200 mL), stirred for 15 minutes, and the layers were separated. The organic layer was washed with water (20 mL), and then with brine (200 mL), dried over Na$_2$SO$_4$, filtered, and evaporated to give 79 g of crude intermediate, 2-bromo-4-t-butylphenol, as an oil.

A solution of crude 2-bromo-4-t-butylphenol in a mixture of acetone (160 mL) and methanol (160 mL) was treated with potassium carbonate (60 g, 433 mmol) and methyl iodide (468 g, 3.3 mol). The mixture was stirred for 3 days at room temperature under N$_2$. The solvents were evaporated, and the residue was partitioned between diethyl ether (350 mL) and water (275 mL). After separation, the organic layer was washed with 20% Na$_2$SO$_3$ (2×100 mL), with water (50 mL), dried over Na$_2$SO$_4$, filtered, evaporated, and dried under high vacuum to give 80.8 g of the title compound as an oil.

Step 2. (4S)-Phenyl-N-(trans-cinnamyl)-2-oxazolidinone. A solution of trans-cinnamic acid (20 g, 135 mmol) in anhydrous tetrahydrofuran (THF) (490 mL) at 0° C. was treated with triethylamine (23.0 mL, 164 mmol) with stirring during 2 minutes. The temperature was lowered to –78° C., and a solution of lithiated (4S)-phenyl-2-oxazolidinone [prepared at –78° C. by treating a solution of (4S)-phenyl-2-oxazolidinone (20 g, 123 mmol) and triphenylmethane (74 mg) in anhydrous THF (490 mL) with 2.5 M n-BuLi in hexane (56 mL) and stirring for 40 minutes] was added via cannula over 1 h. During addition THF (20 mL) was added to redissolve the precipitate. The solution was stirred for 30 minutes at –78° C., and then for 2 hours at 0° C. Saturated aqueous NH$_4$Cl (400 mL) was added slowly, and 15 minutes later, the volatile solvents were removed under vacuum. The residue was mixed with dichloromethane (375 mL), and the aqueous layer was separated. The organic layer was washed with saturated Na$_2$CO$_3$ (2×400 mL) and brine (200 mL), dried over Na$_2$SO$_4$, filtered, evaporated, and dried under high vacuum to give 40.0 g of crude product It was purified by crystallization from ethyl acetate (250 mL). After standing for 3 days, the crystals were collected and washed with 1:1 petroleum ether-ethyl acetate (150 mL) to give 25.1 g (70%) of the title compound as a white solid. The filtrate produced a second crop that weighed 5.36 g (15%).

Step 3. (4S)-Phenyl-(3S)-(2-methoxy-5-t-butylphenyl)-3-phenylpropanoyl-2-oxazolidinone. A solution of 1-methoxy-2-bromo-4-t-butylbenzene (75.4 g, 311 mmol) in anhydrous THF (450 mL) was added dropwise during 2 hours to a stirred solution of activated magnesium (9.08 g, 374 mmol; activated by stirring under high vacuum at 80° C. for 20 minutes) at room temperature under N$_2$. The color turned black, and the mixture was stirred overnight. The supernatant, containing the organomagnesium compound, was added via cannula to a solution of CuBr-dimethylsulfide complex (32 g, 156 mmol) in THF (490 mL) and dimethylsulfide (235 mL) at –40° C. over 70 minutes. When the temperature in the cooling bath reached –25° C. (about 20 minutes), the temperature was reduced to –30° C., and a solution of (4S)-phenyl-N-(trans-cinnamyl)-2-oxazolidinone (30.5 g, 104 mmol) in THF (520 mL) was added dropwise over 75 minutes, with the temperature being maintained between –25 and –35° C. When the addition was complete, the reaction mixture was stirred for 1 hour, over the course of which the reaction slowly warmed to –10° C. Two hours later, the temperature had risen to 5° C. The reaction was quenched by addition of saturated aqueous NH$_4$Cl (800 mL), and the organic solvents were removed under vacuum. The resulting material was treated with ethyl acetate (250 mL), and the layers were separated. The organic layer was washed with 17% NH$_4$OH (4×200 mL), water (100 mL) and then brine (100 mL), dried over Na$_2$SO$_4$, filtered, and evaporated. The resulting red material (87 g) was purified by dissolving in hot ethyl acetate (150 mL), and then slowly adding 6:1 petroleum ether-ethyl acetate (175 mL) with stirring. After 2 hours, petroleum ether (150 mL) was added, and the mixture was stirred overnight. The resulting crystals were collected by suction filtration, washed with petroleum ether (100 mL), and dried under high vacuum to give 37.0 g (78%) of the title compound, mp 159–160° C. A second crop (4.2 g, 8.8%) was obtained by reducing the volume of the filtrate to an oil and treating with petroleum ether (150 mL). $^1$H NMR (300 MHz, CDCl$_3$) δ 7.34–7.04 (m, 12H), 6.75–6.69 (m, 1H), 5.30 (dd, 1H, J=8.6, 3.6 Hz), 4.99 (dd, 1H, J=8.5, 6.9 Hz), 4.56 (t, 1H, J=8.7 Hz), 4.16 (dd, 1H, J 8.8, 3.7 Hz), 3.88–3.70 (m, 2H), 3.67 (s, 9H); $^{13}$C NMR (75 MHz, CDCl$_3$) δ 171.6, 155.3, 154.4, 144.2, 143.6, 139.7, 131.6, 129.6, 128.8, 128.6, 126.7, 126.1, 125.6, 125.6, 124.6, 111.1, 70.4, 58.0, 56.1, 56.0, 40.5, 40.4, 34.7, 32.1.

Step. 4. (3S)-(2-Methoxy-5-t-butylphenyl)-3-phenylpropanoic acid. A solution of (4S)-phenyl-(3S)-(2-methoxy-5-t-butylphenyl)-3-phenylpropanoyl-2-oxazolidinone (37 g, 81 mmol) in a mixture of THF (325 mL) and water (80 mL) was cooled to 0° C., and treated dropwise with an aqueous solution of 30% H$_2$O$_2$ (33.0 mL, 323 mmol) over 10 minutes, followed by dropwise addition of aqueous LiOH (3.87 g, 162 mmol in 202 mL water) over 20 minutes. After stirring at 0° C. for 4 hours, the solution was treated with 1.3 M Na$_2$SO$_3$ (41 g, 323 mmol in 250 mL water). The THF was removed under vacuum, and the aqueous solution contained a suspension of the (4S)-phenyl-2-oxazolidinone product. It was filtered by suction filtration and washed with water (150 mL), then dried under vacuum to give 5.5 g (42%) of the recyclable chiral auxiliary, (4S)-phenyl-2-oxazolidinone. The aqueous filtrate was extracted with dichloromethane (3×50 mL) and then with diethyl ether (150 mL), and the organic extracts were combined and washed with water (3×40 mL). The combined organic extracts were dried over Na$_2$SO$_4$, filtered, evaporated, and the residue crystallized from ethyl acetate to give an additional 2.71 g (20%) of the chiral auxiliary. The aqueous layer was acidified with 6 N HCl (60 mL) to pH 1.0, and then extracted with dichloromethane (3×200 mL). The dichloromethane extracts were combined and washed with water (100 mL), dried over Na$_2$SO$_4$, filtered and evaporated to give 24.6 g of title product. $^1$H NMR (300 MHz, CDCl$_3$) δ 7.25–7.19 (m, 4H), 7.18–7.14 (m, 3H), 6.76–6.73 (m, 1H), 4.86 (t, J=7.9 Hz, 1H), 3.72 (s, 3H), 3.09–3.06 (m, 2H), 1.24 (s, 9H); $^{13}$C-NMR (75 MHz, CDCl$_3$) δ 179.6, 155.4, 143.8, 143.6, 131.5, 129.0, 128.5, 126.9, 125.8, 124.8, 111.0, 56.0, 41.5, 40.3, 34.8, 32.2.

Step 5. (3S)-(2-Methoxy-5-t-butylphenyl)-3-phenylpropanol. A suspension of LiAlH$_4$ (22.3 g, 587 mmol, 8 equivalents) in anhydrous THF (270 mL) was cooled to 0° C., and a solution of (3S)-(2-methoxy-5-t-butylphenyl)-3-phenylpropanoic acid (23.5 g) in anhydrous THF (214 mL) was added via cannula during 20 minutes. The cooling bath was removed, and the mixture was stirred for 3 days at room temperature. The reaction was quenched at 0° C. by the careful, dropwise addition of acetic acid (25 mL) followed by water (10 mL) and 2N HCl (60 mL), and then by 6N HCl (30 mL). The precipitate was filtered with suction and washed with diethyl ether (500 mL). The biphasic filtrate was separated, and the organic layer was washed with 6 N HCl (200 mL). The organic layer was diluted with diethyl ether (100 mL), washed with water (100 mL) and saturated aqueous sodium carbonate (2×100 mL), dried over Na$_2$SO$_4$, filtered and evaporated to give 20.8 g (97%) of the title compound as an oil. $^1$H NMR (300 MHz, CDCl$_3$) δ 7.32–7.10 (m, 7H), 6.81–6.74 (m, 1H), 4.58 (t, J=7.8 Hz, 1H), 3.78 (s, 3H), 3.68–3.49 (m, 2H), 2.41–2.16 (m, 2H), 1.65–1.59 (m, 1H), 1.25 (s, 9H); $^{13}$C NMR (75 MHz, CDCl$_3$) δ 155.5, 145.4, 143.8, 132.9, 128.8, 126.5, 125.7, 124.3, 111.0, 61.6, 56.1, 40.5, 38.5, 34.8, 32.3.

Step 6. (3S)-(2-Methoxy-5-t-butylphenyl)-3-phenylpropyl p-toluenesulfonate. A solution of (3S)-(2-methoxy-5-t-butylphenyl)-3-phenylpropanol (20 g, 68 mmol) in dichloromethane (78 mL) and pyridine (39 mL, 476 mmol) was cooled to 0° C. and treated with p-toluenesulfonyl chloride (16 g, 85 mmol). After stirring for 5 hours, an additional 0.2 equivalents of p-toluenesulfonyl chloride was added, and the mixture was stirred overnight at 00° C. The mixture was treated with ice-water (250 mL) while being stirred vigorously for 90 minutes at room temperature. The organic phase was diluted with dichloromethane (100 mL) and separated. It was then washed with water (2×50 mL), cold 2 N HCl (3×170 mL), water (50 mL), dried over Na$_2$SO$_4$, and placed under vacuum to remove solvents <50° C. The resulting crude oil was treated with petroleum ether (200 mL) and the solvent removed between 30–35° C. to give the title compound as a white solid (30 g, 98%), mp 75–76° C. $^1$H NMR (300 MHz, CDCl$_3$) δ 7.76–7.66 (m, 2H), 7.32–7.05 (m, 9H), 6.75–6.69 (m,1H), 4.41 (t, J=8.1 Hz, 1H), 4.04–3.90 (m, 2H), 3.70 (s, 3H), 2.44–2.28 (m, 2H), 1.24 (s, 9H); $^{13}$C NMR (75 MHz, CDCl$_3$) δ 155.4, 145.1, 144.1, 143.4, 133.8, 131.3, 130.4, 128.9, 128.6, 128.3, 126.7, 125.2, 124.7, 111.1, 69.7, 55.8, 40.06, 34.6, 32.2, 31.7, 21.9.

Step 7. N-Isopropyl-(3S)-(2-methoxy-5-t-butylphenyl)-3-phenylpropylamine. A solution of (3S)-(2-methoxy-5-t-butylphenyl)-3-phenylpropyl p-toluenesulfonate (29 g, 65 mmol) and isopropylamine (110 mL, 1.29 mol) in N,N-dimethylformamide (DMF) (258 mL) was stirred under N$_2$ for 24 hours at room temperature. The solution was concentrated under high vacuum, and the residue was partitioned between dichloromethane (100 mL) and water (50 mL), and the mixture was diluted with diethyl ether (160 mL). The organic layer was separated, washed with water (2×50 mL), 10% K$_2$CO$_3$ (2×50 mL), dried over Na$_2$SO$_4$, filtered and evaporated to give 22 g (100%) of the title compound. $^1$H NMR (300 MHz, CDCl$_3$) δ 7.31–7.09 (m, 7H), 6.78–6.71 (m, 1H), 4.41 (t, J=7.9 Hz, 1H), 3.74 (s, 3H), 2.77–2.44 (m, 3H), 2.28–2.13 (m, 2H), 1.27 (s, 9H), 0.99 (d, J=4.2, 3H), 0.97 (d, J=4.2 Hz, 3H); $^{13}$C NMR (75 MHz, CDCl$_3$) δ 155.3, 145.5, 143.3, 132.9, 128.6, 128.5, 126.2, 125.4, 124.0, 110.6, 55.7, 48.9, 46.5, 42.2, 36.2, 34.6, 32.1, 23.5.

Step 8. S—N-Isopropyl-(2-hydroxy-5-t-butylphenyl)-3-phenylpropylamine. A solution of N-isopropyl-(3S)-(2-methoxy-5-t-butylphenyl)-3-phenylpropylamine (21.1 g, 62.1 mmol) in dichloromethane (138 mL) was cooled to 00° C. and treated dropwise with a 1 M solution of BBr$_3$ in dichloromethane (68.4 mL). After being stirred overnight at 0° C., the brown reaction mixture was carefully quenched with dropwise 2N NaOH (130 mL). The dichloromethane was removed under vacuum, and the remaining suspension was washed with diethyl ether (150 mL). The ethereal layer was washed with 2N NaOH (20 mL) and then with saturated aqueous Na$_2$CO$_3$ (100 mL), dried over Na$_2$SO$_4$, filtered and evaporated giving 18.9 g (93%) of the title compound. $^1$H NMR (300 MHz, CDCl$_3$) δ 7.34–7.28 (m, 4H), 7.24–7.16 (m, 1H), 7.08–7.02 (m, 1H), 6.87–6.81 (m, 1H), 6.71–6.66 (m, 1H), 4.62 (dd, J=12.4, 4.0 Hz, 1H), 2.94–2.76 (m, 2H), 2.50–2.40 (m, 1H), 2.36–2.10 (m, 2H), 1.17 (d, J=6.3 Hz, 3H), 1.13 (d, J=6.3 Hz, 3H), 1.10 (s, 9H); $^{13}$C NMR (75 MHz, CDCl$_3$) δ 154.4, 145.3, 142.9, 131.2, 128.9, 128.6, 126.5, 126.3, 124.4, 117.4, 49.1, 44.1, 40.0, 34.6, 34.5, 32.0, 23.2, 21.8.

Step 9. S—N-Isopropyl-(2-hydroxy-5-t-butylphenyl)-3-phenylpropylamine hydrochloride. A solution of S—N-isopropyl-(2-hydroxy-5-t-butylphenyl)-3-phenylpropylamine (18.9 g, 58.1 mmol) in methylene chloride (250 mL) was treated with a solution of 2N hydrogen chloride in diethyl ether (58 mL, 116 mmol). The solvents were concentrated under vacuum, and the resulting suspension was filtered with suction, and the solid was washed with dichloromethane. The material was dissolved in minimal methanol (70 mL) at room temperature, and concentrated with heat to about half the volume, and then diluted with dichloromethane. After concentration to about half volume, the solution was treated in several portions with a mixture of 4:1 diethyl ether:dichloromethane (100 mL total). The precipitated product was collected by filtration and washed with diethyl ether (200 mL) to give 13.5 g (64%) of the title compound, mp 165–167° C. The second crop weighed 4.0 g (19%), and the third crop weighed 1.0 g (5%). $^1$H NMR (300 MHz, DMSO-d$_6$) δ 7.33–7.26 (m, 4H), 7.20–7.13 (m, 2H), 7.05–6.99 (m, 1H), 6.74–6.68 (m, 1H), 4.34 (t, J=7.9 Hz, 1H), 3.34–3.17 (m, 1H), 2.86–2.63 (m, 2H), 2.43–2.25 (m, 2H), 1.22 (s, 9H), 1.16 (d, J=6.5 Hz, 6H); $^{13}$C NMR (75 MHz, DMSO-d$_6$) δ 152.7, 144.4, 141.4, 129.0, 128.6, 128.1, 126.4, 124.5, 123.9, 115.1, 49.2, 43.1, 41.4, 40.7, 34.1, 31.8, 30.6, 18.9, 18.8. Enantiomeric excess (ee)>99.5% [12 µL of a 5.0 mg/mL solution of the free base (converted from the HCl salt) in 3:1 hexane:EtOH was injected onto a Chiralcel OD 250×4.6 mm column, mobile phase 95:5:0.1 hexane:EtOH:diethylamine, λ 285 nm, flow rate 1 mL/min, r$_t$=5.30 min).

Biological Testing

Compounds of the present invention are tested for the following effects utilizing art accepted methods referred to hereunder:

A. Acute Toxicity in Mice.

The experiments are carried out on conscious albino mice that are administered intravenously or orally with escalating doses of the test compounds.

B. Ligand Binding Studies: Muscarinic Receptors.

The assays are performed using the following methods:

| Receptors | Membranes | Reference Compounds | References |
|---|---|---|---|
| M-1(h) | human recombinant (CHO cells) | pirenzepine | Dorje et al. 1991 |
| M-2(h) | human recombinant (CHO cells) | methctramine | Dorje et al. 1991 |
| M-3(h) | human recombinant (CHO cells) | 4-DAMP | Dorje et al. 1991 |

The experimental conditions are:

| Receptors | Ligands | Conc. | Nonspecific | Incubation |
|---|---|---|---|---|
| M-1 (h) | [$^3$H]pirenzepine | 2 nM | atropine (1 μN) | 60 min/22° C. |
| M-2 (h) | [$^3$H]AF-DX 384 | 2 nM | atropine (1 μN) | 60 min/22° C. |
| M-3 (h) | [$^3$H]4-DAMP | 0.2 nM | atropine (1 μN) | 60 min/22° C. |

C. Binding to Calcium Channels.

The assays are performed using the following methods:

| Receptors | Membranes | Reference Compounds | References |
|---|---|---|---|
| Ca channel (diltiazem site) | rat cerebral cortex | diltiazem | Schoemaker & Langer (1985) |
| Ca channel (DHP site) | rat cerebral cortex | nitrendipine | Lee et al. (1984) |

The experimental conditions are:

| Receptors | Ligands | Conc. | Nonspecific | Incubation |
|---|---|---|---|---|
| Ca channel (diltiazem site) | $^3$H diltiazem | 5 nM | diltiazem (10 μM) | 120 min 25° C. |
| Ca channel (DHP site) | $^3$H (+) PN200-110 | 0.04 nM | nifedipine (1 μM) | 90 min 22° C. |

After incubation with the test article and the proper radioligand and washing, bound radioactivity is determined by liquid scintillation, using a commercial scintillation cocktail. The specific radioligand binding to each receptor is defined as the difference between total binding and nonspecific binding in the presence of an excess of unlabelled ligand. $IC_{50}$ values (concentrations required to inhibit 59% of specific binding) are determined by non linear regression analysis of the competition curves. These parameters are obtained by curve fitting using Sigmaplot™ software.

Since the compounds of the invention have antihistaminic activity, similar receptor binding tests to those described above are conducted to obtain detailed information regarding binding to the various histaminic receptor types (Chang et al. J. Neurochem. 1979, 32: 1653–1663).

D. Functional Characterization of Antimuscarinic/Antispasmodic Activity—In vitro Studies Urinary bladder smooth muscle strips. Experiments are performed using methods similar to those described by Smith et al. 1998 (Arzneim.-Forsch/Drug Res 48: 1012–1018). Strips of urinary bladders (approximately 10 mm long and 1.5 mm wide) are removed from guinea pigs (males; 400–600 g.) The tissues are suspended in an oxygenated buffer of the following composition, in mM: NaCl, 133; KCl, 4.7; $CaCl_2$, 2.5; $MgSO_4$, 0.6; $NaH_2PO_4$, 1.3; $NaHCO_3$, 16.3; and glucose, 7.7. They are maintained at 37.5° C. Contractions are induced by carbachol or a high potassium concentration in the bath fluid as described below. The smooth muscle contractions are measured with isometric transducers and contractions are recorded and stored electronically.

In each experiment up to six strips are suspended in individual tissue chambers and allowed to equilibrate with the bathing solution for at least 30 min before proceeding with the experiment. The inhibition is expressed as $IC_{50}$ or percent.

Kidney smooth muscle tissues and gall bladder smooth muscle strips. The experiments are performed using the methodology as described for urinary bladder smooth muscle tissues hereinabove.

In each experiment up to six strips are suspended in individual tissue chambers and allowed to equilibrate with the bathing solution for at least 30 min before proceeding with the experiment. The smooth muscle contractions are measured with isometric transducers and contractions are recorded and stored electronically. The inhibition is expressed as IC50 or percent.

Intestinal smooth muscle strips. Experiments are performed using methods similar to those described by Aberg et al. 1965 (Acta Physiol Scand 64: 15–27). Strips of caecum, ileum or taenia coli (approximately 6 mm long and 1 mm wide) are removed from guinea pigs (males; 400–600 g.) The tissues are suspended in an oxygenated buffer of the following composition, in mM: NaCl, 133; KCl, 4.7; $CaCl_2$, 2.5; $MgSO_4$, 0.6; $NaH_2PO_4$, 1.3; $NaHCO_3$, 16.3; and glucose, 7.7. They are maintained at 37° to 38° C. The smooth muscle contractions are measured with isometric transducers and contractions are recorded and stored electronically. The inhibition is expressed as IC50 or percent.

Bronchial smooth muscle strips. Experiments are performed using methods similar to those described by Johansson et al. 1996 (Clin. Rev. Allerg & Asthma, 14: 57–64). Strips of bronchial smooth muscle are removed from guinea pigs (males; 400–600 g.) The tissues are suspended in an oxygenated buffer of the following composition, in mM: NaCl, 133; KCl, 4.7; $CaCl_2$, 2.5; $MgSO_4$, 0.6; $NaH_2PO_4$, 1.3; $NaHCO_3$, 16.3; and glucose, 7.7. They are maintained at 370 to 38° C. Contractions are induced as described by Johansson et al (see above). The smooth muscle contractions are measured with isometric transducers and contractions are recorded and stored electronically. The inhibition is expressed as IC50 or percent.

In each experiment up to six preparations are suspended in individual tissue chambers and allowed to equilibrate with the bathing solution for at least 30 min before proceeding with the experiment. The inhibition is expressed as IC50 or percent.

Uterine smooth muscle strips. Isolated uterus preparations (approximately 6 mm long and 1 mm wide) from rats are contracted with 0.003 μM oxytocin and the contractions are reduced with the test articles and compared to the effects of reference calcium antagonist, such as nifedipine. Contractions can also be induced by carbachol or a high potassium concentration in the bath fluid.

In each experiment up to six strips are suspended in individual tissue chambers and allowed to equilibrate with the bathing solution for at least 30 min before proceeding with the experiment. The inhibition is expressed as IC50 or percent.

Carbachol- and potassium-induced contractions. In order to assess the viability of each tissue and to serve as a frame of reference, contractions of each strip of tissue are recorded initially in response to exposure to tissue medium in which the NaCl was replaced by KCl to yield a concentration of 137.7 mM KCl in the medium. This is followed by return to the standard medium, and then by exposures to progressively in creasing concentrations of carbachol, with separate exposures to each concentration only until the peak response has been recorded. The effects of increasing concentrations of the test article on contractions induced by 137.7 mM KCl are recorded in separate experiments. IC50 values or pA2 values or inhibition expressed in percent are calculated using conventional statistic methodology.

E. Functional Characterizations of Antispasmodic Activity—In vivo Studies

The test method used in the present in vivo evaluations measures effects of test articles on induced hyperactivity of the urinary bladder of rats. In vivo rhythmic contractions of the urinary bladder are studied in urethane-anesthetized (1.2 g/kg, sc), male Wistar-Kyoto rats (300–500 g). Body temperature is maintained using a heated blanket. The bladder is exposed through a midline incision of the abdomen and a balloon is inserted into the bladder. Warm water of 37° C. is injected into the balloon and bladder volume was maintained at 1.0 to 1.5 ml, depending on bladder size. The spontaneous contractions are recorded using a pressure transducer connected to the balloon. When the frequency and the amplitude of the bladder contractions reached constant levels, the test article is administered intravenously. Cardiovascular parameters are measured simultaneously with the effects on the bladder motility or were studied in separate experiments. All parameters are recorded and stored electronically.

F. Effects on the QT-interval of the ECG

Anesthetized male guinea pigs (450–600 g) are used. The trachea is cannulated. Lead II electrocardiogram are recorded at 50 mm/sec. The is a 30 minute stabilization time after surgery, during which three baseline EKG recordings are made at 10-min intervals. Test article or vehicle are administered as an iv infusion over 30 min. ECG recordings are used to determine QT intervals and heart rates. To compensate for variations in heart rates, QTc intervals are calculated from QT- and RR-intervals as known to those skilled in the art. Prolongation of QTc is indicative of a prolonged action potential. Prolongation of QTc is a known cause of Torsades de Pointes ventricular fibrillation by drugs such as terodiline, terfenadine and astemizole (all of which have been withdrawn because of arrhythmogenic side effect).

G. Cardiovascular Effects in vivo

Studies were performed in anesthetized rats, being administered the test substances intravenously. Effects on arterial blood pressure were recorder through an arterial catheter and a pressure recorder, while effects on heart rate were calculated from the ECG.

Clinical Doses of Compounds of the Present Invention

The magnitude of a prophylactic or therapeutic dose of the compounds of this invention in the acute or chronic management of disease will vary with the severity and nature of the condition to be treated and the route of administration. The dose and the frequency of the dosing will also vary according to the age, body weight and response of the individual patient. In general, the total daily dose range for the compounds of this invention for the conditions described herein is from about 0.5 mg to about 200 mg as single, divided or multiple doses. Compounds with a long biological half-life can be given once or twice daily. In managing the patient, the therapy can be initiated at a lower dose, of 0.5 mg to about 50 mg, and may be increased up to 200 mg depending on the patient's global response. It is further recommended that patients over 65 years and those with impaired renal or hepatic function initially receive low doses and that they be titrated based on individual response(s) and plasma drug level(s). It may be necessary to use dosages outside these ranges, as will be apparent to those skilled in the art. Further, it is noted that the clinician or treating physician will know how and when to interrupt, adjust, or terminate therapy in conjunction with individual patient response. The terms "a therapeutically effective amount" and "an amount sufficient to treat incontinence but insufficient to cause adverse effects" are encompassed by the above-described dosage amounts and dose frequency schedule.

Routes of Administration of the Present Invention

Any suitable route of administration may be employed for providing the patient with an effective dosage of the compounds of this invention. For example, oral, sublingual, rectal, vaginal, parenteral (subcutaneous, intramuscular, intraarterial, intravenous), transdermal, by inhalation and like forms of administration may be employed. Additionally, solutions containing the drug may be administered directly into the bladder through the urethra. Dosage forms include tablets, troches, suspensions, solutions, capsules, microencapsulated systems, aerosols, various transdermal delivery systems, and the like.

Pharmaceutical Compositions of the Present Invention

The pharmaceutical compositions of the present invention comprise at least one compound of the present invention as the active ingredient, or a pharmaceutically acceptable salt thereof, and may also contain a pharmaceutically acceptable carrier, and optionally, other therapeutic ingredients.

The terms "pharmaceutically acceptable salts" or "a pharmaceutically acceptable salt thereof" refer to salts prepared from pharmaceutically acceptable non-toxic acids or bases. Examples of suitable pharmaceutically acceptable acid addition salts for the compounds of the present invention include acetic, benzenesulfonic (besylate), benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pathothenic, phosphoric, p-toluenesulfonic, succinic, sulfuric, tartaric, and the like. Examples of such bases include metallic salts made from aluminum, calcium, lithium, magnesium, potassium, sodium, and zinc, while appropriate organic bases may be selected, for example from N,N'-dibenzylethylenediamine, chloroprocaine, choline, diethanolamine, ethylenediamine, meglumaine (N-methylglucamine), lysine and procaine.

The compositions of the present invention include suspensions, solutions, elixirs, crèmes, gels, ointments, aerosols or solid dosage forms. Carriers such as starches, sugars, and microcrystalline cellulose, diluents, granulating agents, lubricants, binders, disintegrating agents, and the like are suitable in the case of oral solid preparations (such as powders, capsules, and tablets), and oral solid preparations are preferred over the oral liquid preparations for administration to adults, while oral liquid preparations may be preferred for administration to children.

Because of their ease of administration, tablets and capsules represent two of the more advantageous oral dosage unit forms, in which cases solid pharmaceutical carriers are employed. If desired, tablets may be coated by standard aqueous or non-aqueous techniques. The oral dosage forms may be designed to release the active ingredient in a controlled manner, for example slow-release tablets or delayed-release tablets or capsules. Such controlled release dosage forms are particularly useful in cases where the therapeutically active compound has a short biological half-life, as may be the case for some compounds of this invention.

In addition to the common dosage forms set out above, the compounds of the present invention may also be administered by controlled release means and delivery devices such as those described in U.S. Pat. Nos. 3,845,770; 3,916,899; 3,536,809; 3,598,123; and 4,008,719, and PCT application WO92/20377, the disclosures of which are hereby incorporated by reference.

Pharmaceutical compositions of the present invention suitable for oral administration may be presented as discrete unit dosage forms intended for instant release or for controlled or delayed release such as capsules, cachets, or tablets, each containing a predetermined amount of the active ingredient, as a powder or granules, or as a solution or a suspension in an aqueous liquid, a non-aqueous liquid, an oil-in-water emulsion, or a water-in-oil liquid emulsion. Such compositions may be prepared by any of the methods of pharmacy, but all methods include the step of bringing into association the active ingredient with the carrier, which constitutes one or more necessary ingredients. In general, the compositions are prepared by uniformly and intimately admixing the active ingredient with liquid carriers or finely divided solid carriers or both, and then, if necessary, shaping the product into the desired presentation.

For example, a tablet may be prepared by compression or molding, optionally, with one or more accessory ingredients, as shown below:

| ORAL FORMULATION - TABLETS | | |
|---|---|---|
| | Quantity per tablet in mg | |
| Ingredients | A | B |
| Active ingredient according to Example 14 | 5.0 | 20.0 |
| Lactose BP | 148.5 | 133.5 |
| Starch BP | 30.0 | 30.0 |
| Pregelatinized Maize Starch BP | 15.0 | 15.0 |
| Magnesium stearate | 1.5 | 1.5 |
| Compression weight | 200.0 | 200.0 |

Compressed tablets may be prepared by compressing in a suitable machine the active ingredient in a free-flowing form such as powder or granules, optionally mixed with a binder, lubricant, inert diluent, surface active agent or dispersing agent. Molded tablets may be made by molding, in a suitable machine, a mixture of the powdered compound moistened with an inert liquid diluent. All of the foregoing techniques are well know to persons of skill in the pharmaceutical art. Each tablet may contain from about 0.1 mg to about 200 mg of the active ingredient. Slow-release or controlled-release tablets may contain up to 500 mg of the active ingredient.

The active ingredient is sieved through a suitable sieve and blended with the lactose until a uniform blend is formed. Suitable volumes of water are added and the powders are granulated. After drying, the granules are then screened and blended with the magnesium stearate. The resulting granules are then compressed into tablets of desired shape. Tablets of other strengths may be prepared by altering the fill weight and if necessary, changing the tablet weight to suit.

| ORAL FORMULATION - CAPSULES | | |
|---|---|---|
| | Quantity per Capsule in mg | |
| Formula | A | B |
| Active ingredient according to Example 15 | 5.0 | 20.0 |
| Starch 1500 | 94.0 | 79.0 |
| Magnesium Stearate BP | 1.0 | 1.0 |
| Total Weight | 100.0 | 100.0 |

The active ingredient is sieved and blended with the excipients. The mixture is filled into suitably sized two-piece hard gelatin capsules using suitable machinery. Other doses may be prepared by altering the fill weight and if necessary, changing the capsule weight to suit.

Equivalents

Those skilled in the art will recognize, or be able to ascertain, using no more than routine experimentation, many equivalents to the specific embodiments of the invention described herein. Such equivalents include numerous pharmaceutically acceptable salt forms e.g. sulfate, fumarate, hydrobromide, hydrochloride, dihydrochloride, methanesulphonate, hydroxynaphthoate, chlorotheophylline or where appropriate one or other of the hydrate forms thereof, see Merck Index 11th edition (1989) items 9089, 209, 3927, 4628, 8223, 5053, 5836, 8142, 2347, 7765, 1840, 9720, 7461, 1317, 4159, and 963 and references cited therein and Am. Rev. Resp. Dis. 1988, 137: (4;2/2) 32. Such equivalents also include the simultaneous administration of the compound of the present invention with any other drug that is used to combat diseases in mammals. Such equivalents also include the co-administration of the compound of the present invention with any other compound or drug that may be used in combination with medication for urinary incontinence or intestinal hyperactivity, airway obstructive diseases, urolithiasis, cholelithiasis, choledocholithiasis or other forms of smooth muscle hyperactivity or hyperreactivity. Those skilled in the art of medicine will also realize that higher or lower doses than those indicated here may be preferred and the doses may be given more or less frequently than suggested here.

Those skilled in the art of medicine, will realize that the terms intestinal hyperactivity and intestinal hypermotility disorders include diarrhea and irritable bowel syndromes (IBS).

We claim:
1. A compound having the formula:

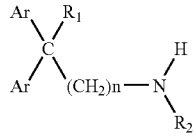

including stereochemically isomeric forms thereof and pharmaceutically acceptable salts thereof, wherein
each Ar represents a phenyl group, at least one of which is substituted with A and B,
A being n-propyl, isopropyl, butyl, isobutyl, sec-butyl, t-butyl,
hydroxypropyl or hydroxybutyl, and
B being hydroxy or lower (1–3) alkoxy;
$R_1$ is hydrogen or lower alkyl;
$R_2$ is methyl, ethyl, n-propyl, isopropyl, butyl, isobutyl, sec-butyl or t-butyl, and
n is 2–4.

2. A compound according to claim 1, wherein each Ar represents a phenyl group, one of which is substituted at the 2-position with a hydroxy group and at the 5-position with a t-butyl group, $R_1$ is hydrogen, $R_2$ is isopropyl and n is 2.

3. The S-isomer of a compound according to claim 1, wherein each Ar represents a phenyl group, one of which is substituted at the 2-position with a hydroxy group and at the 5-position with a t-butyl group, $R_1$ is hydrogen, $R_2$ is isopropyl and n is 2.

4. The R-isomer of compound according to claim 1, wherein each Ar represents a phenyl group, one of which is substituted at the 2-position with a hydroxy group and at the 5-position with a t-butyl group, $R_1$ is hydrogen, $R_2$ is isopropyl and n is 2.

5. A method of treatment or prevention of smooth muscle hyperactivity in a mammal, which comprises administering to said mammal a pharmacologically effective amount of a compound of the formula:

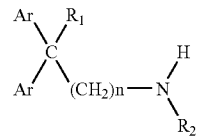

including stereochemically isomeric forms thereof and pharmaceutically acceptable salts thereof, wherein
each Ar represents a phenyl group, at least one of which is substituted with A and B,
A being n-propyl, isopropyl, butyl, isobutyl, sec-butyl, t-butyl,
hydroxypropyl, hydroxybutyl, and
B being hydroxy or lower (1–3) alkoxy;
$R_1$ is hydrogen or lower alkyl;
$R_2$ is methyl, ethyl, n-propyl, isopropyl, butyl, isobutyl, sec-butyl or t-butyl, and
n is 2–4.

6. The method of claim 5, wherein said smooth muscle hyperactivity is the cause of urinary incontinence.

7. The method of claim 5, wherein said smooth muscle hyperactivity is the cause of urinary urge incontinence.

8. The method of claim 5, wherein said smooth muscle hyperactivity is intestinal smooth muscle hyperactivity.

9. The method of claim 5, wherein said smooth muscle hyperreactivity is respiratory smooth muscle hyperactivity.

10. The method of claim 5, wherein said smooth muscle hyperactivity is the cause of urolithiasis.

11. The method of claim 5, wherein said smooth muscle hyperactivity is the cause of cholelithiasis or choledocholithiasis.

12. The method of claim 5, wherein said compound or pharmaceutically acceptable salt thereof is administered in an amount of from 0.5 mg to about 200 mg, one to four times daily.

13. The method of claim 5, wherein said compound or pharmaceutically acceptable salt thereof is administered orally, parenterally, transdermally, ocularly, rectally, vaginally or by inhalation.

14. A pharmaceutical composition comprising a compound having the formula:

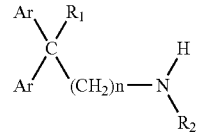

including stereochemically isomeric forms thereof and pharmaceutically acceptable salts thereof, wherein:
each Ar represents a phenyl group, at least one of which is substituted with A and B,
A being n-propyl, isopropyl, butyl, isobutyl, sec-butyl, t-butyl,
hydroxypropyl, hydroxybutyl, and
B being hydroxy or lower (1–3) alkoxy;
$R_1$ is hydrogen or lower alkyl;
$R_2$ is methyl, ethyl, n-propyl, isopropyl, butyl, isobutyl, sec-butyl or t-butyl, and
n is 2–4, together with a pharmaceutically acceptable carrier.

15. A pharmaceutical composition of claim 14, wherein said composition also contains one or more active ingredient selected from the group consisting of anticholinergic drugs, calcium antagonistic drugs, potassium channel activating drugs, adrenergic beta-agonistic drugs, adrenergic alpha-agonistic drugs, analgesic drugs, anti-inflammatory drugs, antihistaminic drugs and local anesthetic drugs.

16. A method for treating smooth muscle hyperactivity in a mammal while reducing concomitant liability of adverse effects associated with the racemic mixture and the (R)-isomer, comprising administering to said mammal a pharmaceutical composition of claim 14, comprising a therapeutically effective amount of the optically pure (S)-isomer of said compound or a pharmaceutically acceptable salt thereof.

17. A method for treating mixed cholinergically and non-cholinergically mediated smooth muscle hyperactivity in a mammal, comprising administering to said mammal a pharmaceutical composition of claim 14, comprising a therapeutically effective amount of said compound in racemic form or the optically pure (R)-isomer of said compound or a pharmaceutically acceptable salt thereof.

* * * * *